US007258972B2

(12) United States Patent
Reymond et al.

(10) Patent No.: US 7,258,972 B2
(45) Date of Patent: Aug. 21, 2007

(54) PROCESS FOR GENERATING THE IDIOSYNCRATIC CATALYTIC IMPRINT OF A SAMPLE, THE PROCESSING OF SAID IMPRINT AND THE SYSTEMS FOR IMPLEMENTATION THEREOF

(75) Inventors: Jean-Louis Reymond, Bulle (CH); Denis Wahler, Nimes (FR)

(73) Assignees: Proteus, Nimes (FR); Universite de Berne, Berne (CH)

( * ) Notice: Subject to any disclaimer, the term of this patent is extended or adjusted under 35 U.S.C. 154(b) by 0 days.

(21) Appl. No.: 10/841,568

(22) Filed: May 10, 2004

(65) Prior Publication Data

US 2005/0009098 A1    Jan. 13, 2005

Related U.S. Application Data

(63) Continuation of application No. PCT/FR02/03827, filed on Nov. 7, 2002.

(51) Int. Cl.
*C12Q 1/00* (2006.01)
(52) U.S. Cl. .......................................... 435/4
(58) Field of Classification Search ...... None
See application file for complete search history.

(56) References Cited

U.S. PATENT DOCUMENTS 4,603,108 A    7/1986  Bascomb

FOREIGN PATENT DOCUMENTS

| EP | 0 451 775 A1 | 10/1991 |
| WO | WO 01/36662 A2 | 5/2001 |
| WO | WO 01/60986 A2 | 8/2001 |
| WO | WO 01/61041 A2 | 8/2001 |

OTHER PUBLICATIONS

Gruninger-Leitch et al. (2000). "Identification of beta-secretase-like activity using a mass spectrometry-based assay system," Nature Biotechnology vol. 18, pp. 66-70.*
Moris-Varas et al. (1999). "Visualization of enzyme-catalyzed reactions using pH indicators: rapid screening of hydrolase libraries and estimation of the enantioselectivity," Bioorganic and Medicinal Chemistry vol. 7, pp. 2183-2188.*
Badalassi et al. (2000). "A versatile periodate-coupled fluorogenic assay for hydrolytic enzymes," Angew. Chem. Int. Ed. vol. 39, pp. 4067-4070.*
Harris, Jennifer et al., "Rapid and general profiling of protease specificity by using combinatorial fluorogenic substrate libraries", PNAS (Jul. 5, 2000), pp. 7754-7759, vol. 97, No. 14.
O'Brien, M. et al., "Enzymatic Profile of *Pseudomonas maltophilia*", Journal of Clinical Microbiology (Sep. 1982), pp. 417-421, vol. 16, No. 3.
International Search Report dated Apr. 4, 2003 for Application No. PCT/FR02/03827.

* cited by examiner

*Primary Examiner*—Sandra E. Saucier
(74) *Attorney, Agent, or Firm*—Hunton & Williams LLP

(57) ABSTRACT

This invention has as its object a process for generating the idiosyncratic catalytic imprint of a sample, characterized in that it comprises the following stages: the sample that is likely to have the catalytic activity is brought into contact with a group of substrates; the signals that are generated after said contact are captured in some way. Advantageously, after the signals are captured, a processing of the latter that consists of assigning to each signal a digital value constituting a component of a graphic display, for example a color display, of the idiosyncratic imprint is carried out.

28 Claims, 25 Drawing Sheets
(9 of 25 Drawing Sheet(s) Filed in Color)

Dark Green Color

Clear Color

Dark Red Color

Light Red Color

Key to Figure 7 :

Coulers = Colors
Personnalisees = Personalized
Teinte = Tint
Sat = Saturation
Lum = Light
Rouge = Red
Vert = Green
Bleu = Blue
Annuler = Cancel
Nouvelle = New
Actuelle = Current
Translucide = Translucent Figure 11
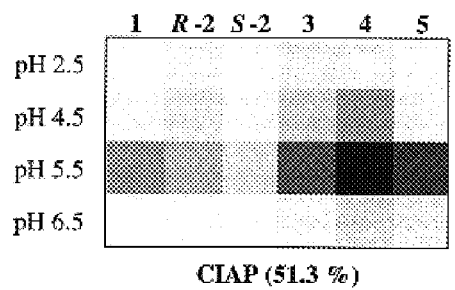
CIAP (51.3 %)
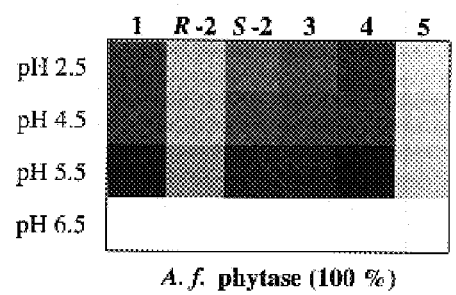
A. f. phytase (100 %)
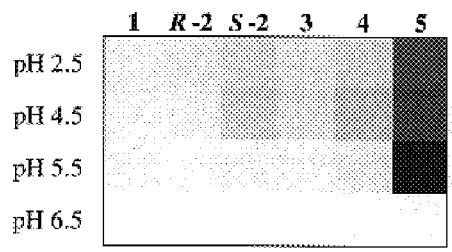
Novo phytase (46.6 %)
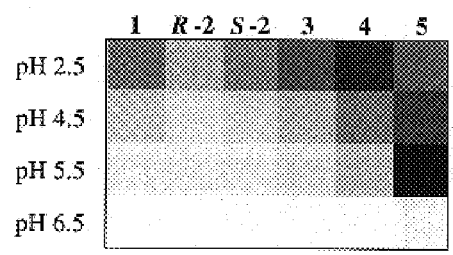
Natuphos phytase (51.5 %)

Figure 17
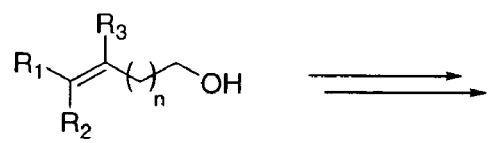
| $R_1, R_2, R_3$ | | n = 0, 1, 2, 3, 4 |
| --- | --- | --- |
| H, H, H | 1 | a, b, c, d, e |
| H, H, Me | 2 | |
| Me, Me, H | 3 | |
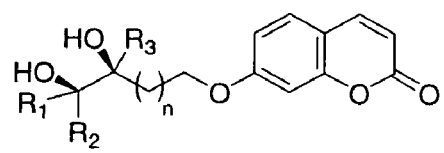
(R)-4
(R)-5
(R)-6
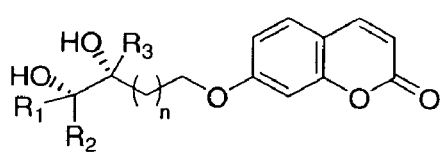
(S)-4
(S)-5
(S)-6
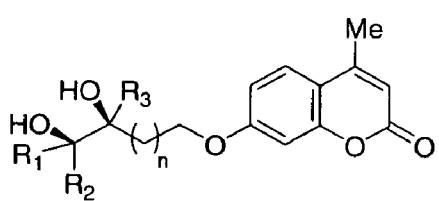
(R)-7
(R)-8
(R)-9
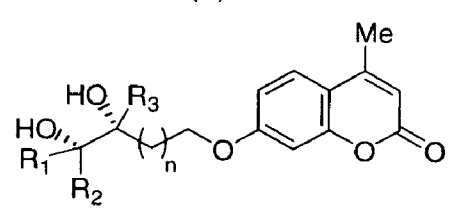
(S)-7
(S)-8
(S)-9

Figure 21
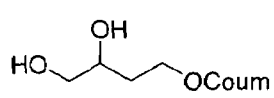
26
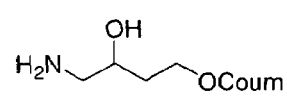
27
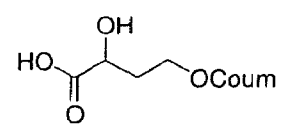
28
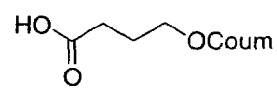
29
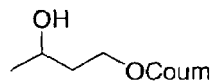
30
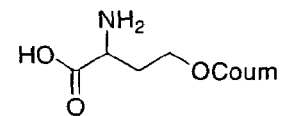
31

Figure 24
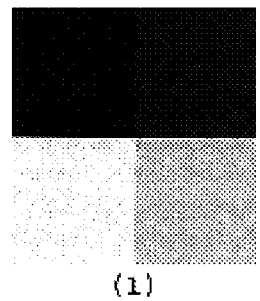
(1)
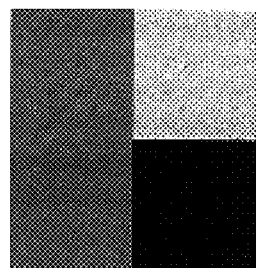
(2)
| $t_r = 10.7$ min | $t_r = 12.8$ min |
|---|---|
| $t_r = 14.6$ min | $t_r = 15.9$ min |

PROCESS FOR GENERATING THE IDIOSYNCRATIC CATALYTIC IMPRINT OF A SAMPLE, THE PROCESSING OF SAID IMPRINT AND THE SYSTEMS FOR IMPLEMENTATION THEREOF

CROSS-RELATED AND PRIORITY APPLICATIONS

The present application is a continuation of International Application No. PCT/FR02/03827, filed Nov. 7, 2002, which claims the benefit of French Patent Application No. 01/14462, filed Nov. 8, 2001 and French Patent Application No. 02/08633, filed Jul. 9, 2002. The disclosures of these priority applications are hereby incorporated by reference in their entirety.

FIELD OF INVENTION

This invention relates to a process that makes it possible to generate an idiosyncratic catalytic imprint of a sample. The invention also relates to systems for the implementation of such a process and use thereof.

BACKGROUND OF INVENTION

A sample may exhibit various catalytic characteristics. They are expressed by, for example, different enzymatic classes.

In the prior art, the use of the same type of substrates that makes it possible to develop a given enzyme is known.

It is possible to cite those that relate to the determination of the better substrate of a specific protease (PNAS 97 (14), 7754–7759 and Nature Biotechnology 28, 187–193). This technique consists in testing banks of several thousands to several hundreds of thousands of substrates solely of peptide type with a known protease. This is limited to cases of proteases because the protein substrates are synthesized by combinatory chemistry.

It is also possible to cite the detection of microorganisms (Patent U.S. Pat. No. 4,603,108; Patent EP 451 775; J. Clin. Microbiol (1982), 16 (3), 417–21). These techniques are based on the detection of enzymes for identifying microorganisms whose characteristics are already known.

The PCT Patent Application published under No. WO01/60986 relates to the esterases that have a particular activity. The identification of these esterases is made by comparison to reference esterase profiles carried out in advance on esterase substrates. It is a matter of seeking the best enzyme for a given substrate type. These substrates correspond only to ester functions.

SUMMARY OF INVENTION

This invention has as its object to remedy the drawbacks of the techniques of the prior art by offering a process that makes it possible to generate the idiosyncratic catalytic imprint of a sample, i.e., its specific identity card.

The invention therefore has as its object a process for generating an idiosyncratic catalytic imprint of a sample, wherein the process comprises:
  a) The sample that is likely to have the catalytic activity is brought into contact with a group of substrates,
  b) The signals that are generated after said contact are captured.

The process of the invention is remarkable in that this imprint may be obtained without knowing the catalytic activities of the sample.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 6 shows stages of processing values to form a color imprint of a catalytic activity. In particular.

FIG. 11 shows idiosyncratic imprints, as well as maximum conversion percentages.

FIG. 17 shows a series of 1,2-diols of various structures that can be analyzed by HPLC.

FIG. 21 shows a series of products exhibiting a variety of functional groups for an analysis by HPLC of a mixture of the latter.

FIG. 24 shows idiosyncratic imprints of *Mucor Miehei* esterase (1) and *Pseudomonas Fluorescens* lipase (2).

DETAILED DESCRIPTION OF PREFERRED EMBODIMENTS

Figures 1A, 1B:
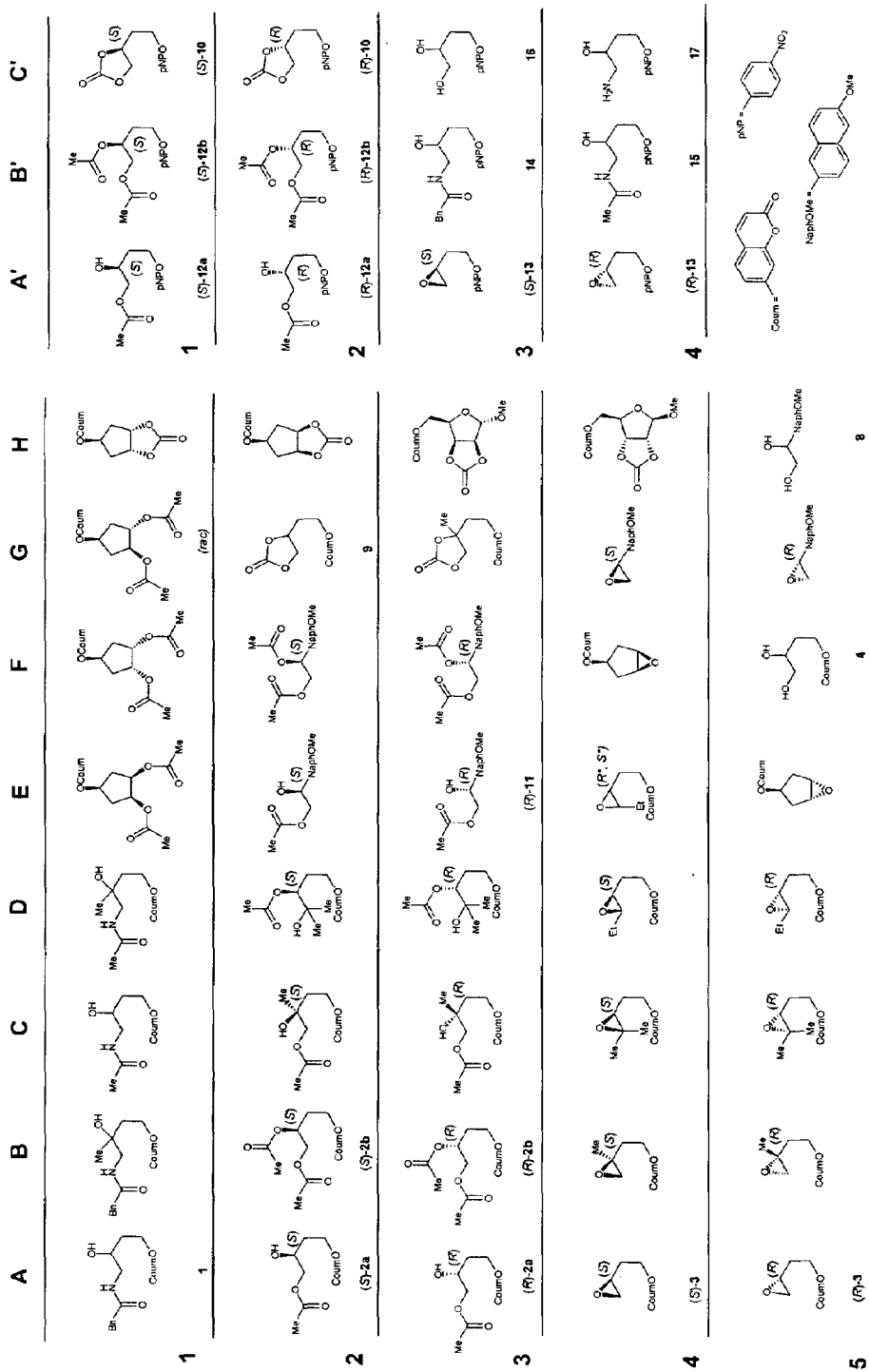
FIG. 1 shows examples of formulas of fluorogenic substrates (FIG. 1a), and chromogenic substrates (FIG. 1b) that are useful according to the invention.

In stage (a), the substrates can be ordered or can be in the form of a mixture. "Idiosyncratic catalytic imprint", according to the invention, is defined as an individual image or identity card of catalytic activities. This imprint is specific to a sample. It is obtained after the sample is brought into contact with a group of substrates. The idiosyncratic imprint combines measures that are carried out on different substrates. The idiosyncratic catalytic imprint testifies to an identity of a sample in the form of a display of a sample that has reacted with a group of substrates.

"Idiosyncratic" is defined as the individual capacity of a sample to react with a group of substrates.

"Catalytic activity" is defined as any activity of a sample that can modify a substrate. This activity may correspond to, for example, that of one or mote proteins, DNA molecules, RNA molecules or a mixture of the latter. Advantageously, this activity corresponds to that of an enzyme or a mixture of enzymes. These activities can also be those of recombinant products that are obtained by genetic engineering.

These activities can correspond to, for example, hydrolases, oxidoreductases, transferases, lyases, isomerases and ligases.

The catalytic activity that is defined in terms of the invention can correspond to a mixture of activities; it can be known or unknown.

The sample can be obtained from various origins. It can be, for example, chemical, biological, microbiological, animal, vegetable or human. It can be obtained from all types of environments and from sampling.

The sample can be simple or complex, prepared from standard extraction techniques, then optionally purified or used just as is.

According to a first implementation, in stage (a), the contact is carried out with a group of ordered substrates. Thus, in this embodiment, the capture of the signals is done in an ordered way according to the organization of the group of substrates.

According to a second implementation, in stage (b), the signals are captured in an ordered way.

After the capture of signals, the process of the invention comprises a stage for processing the captured signals comprising assigning to each signal a digital value that constitutes a component of a graphic display, for example, a color display, of the idiosyncratic imprint.

This processing can be applied to any signal or to a combination of signals that are obtained from the same group of substrates or several groups of substrates. It is then a matter of assigning to each signal a digital value, then in associating per group of at least two values the digital values that are obtained from the same group of substrates or several groups of substrates and to assign to each group a digital value that constitutes a component of a graphic display, for example a color display, of an idiosyncratic imprint.

Such a processing makes it possible, for example, to combine several imprints so as to generate a new imprint, and to obtain a graphic display, most particularly in colors facilitating the visualization, and therefore the operation, of accumulated characteristics of a sample. Thus, the processing of the imprints can include a color display of the new imprint of the type that is based on the RGB (red, green, blue) system.

After contact with the sample that is likely to have catalytic activity, the substrates may either remain intact or be transformed into one or more products. The substrates and/or products that are obtained after contact with the sample can be ordered or can be in the form of a mixture.

According to the first embodiment above, the substrates are ordered on a support, such as, for example, on a microtitration plate or a microsystem. This support that has all of the substrates may constitute a system that is used for generating the idiosyncratic catalytic imprint according to the process of the invention. In some particular cases, it is possible to have substrates that are placed on several supports.

The invention thus relates to a process for generating the idiosyncratic catalytic imprint of a sample that comprises the following stages:
 a) The sample that is likely to have catalytic activity is brought into contact with a group of ordered substrates,
 b) The signals that are generated after said contact are captured.

According to the second embodiment above, the substrates are mixed, and the capture of the signals is carried out in an ordered way.

The signals can be ordered by using a separation technique such as HPLC (High-Pressure Liquid Chromatography), TLC (Thin-Layer Chromatography) or MS (Mass Spectrometry).

The invention thus relates to a process for generating the idiosyncratic catalytic imprint of a sample, comprising the following stages:
 a) The sample that is likely to have catalytic activity is brought into contact with a group of substrates in the form of a mixture,
 b) The signals that are generated after said contact are captured in an ordered way. In this embodiment, the signals that are generated after said contact are captured in an ordered way by using a separation technique such as HPLC.

Each substrate comprises at least one functional group that is sensitive to the presence of a catalytic activity of a sample and makes possible the generation of a signal directly or indirectly.

A substrate that is implemented in the process of the invention is any molecule that comprises at least one functional group that is sensitive to the presence of a catalytic activity and that makes possible the generation of a signal.

The functional groups correspond by way of nonlimiting examples to:
 Ester group, suitable for lipases, esterases, and peptidases;
 Carbonate group, suitable for lipases, esterases, and peptidases;
 Carbamate group, suitable for peptidases;
 Amide group, suitable for peptidases;
 Lactam group, suitable for peptidases and lactamases;
 Epoxide group, suitable for hydrolases, in particular epoxide hydrolases;
 Phosphate group, suitable for phosphatases and phytases;
 Glycoside group, suitable for glycosidases;
 Ether, alkene and alkane groups that are suitable for monoxygenases and hydroxylases;
 Alcohol group that is suitable for dehydrogenase alcohols; and/or
 Aldol group that is suitable for aldolases.

In addition to the functional groups above that define catalytic activities, each substrate can comprise a chemical group that is likely to impart to it a specificity for an activity defined by the functional group. In a preferred embodiment, these chemical groups consist of substitution variations. The nature of the variations will preferably be on the order of:

Steric, such as, for example, different alkyl or aryl groups; or

Stereochemical; or else

Electronic, such as, for example, electron donor groups or electron attractor groups.

Variations of stereochemical order thus make it possible to use separately each enantiomer of a pair of enantiomers, more generally each of the stereoisomers of a group of stereoisomers.

The substrates also make possible the generation of a signal in a direct or indirect manner. A direct signal is defined as all signals that are obtained directly after contact of the substrate with the sample.

Indirect signals are defined as all signals that are obtained after one or more reactions, in particular chemical reactions, after contact of the substrate with the sample.

The signals that are emitted are based on the nature of the substrate and/or the selected detection system as well as measuring conditions. They can be of different types, in particular spectrophotometric (absorbence or fluorescence of light at a given wavelength), electrical or chemical types. Substrates of chromogenic or fluorogenic type are preferably used. It is also possible, however, to record the course of the reaction on any substrate by suitable outside sensors, such as a thermometric probe, a pM indicator, a protein-type product sensor (anti-product antibody) or synthetic chemosensor, or a measurement coupled to secondary enzymes. It is possible to cite as an example the dehydrogenase alcohol for detecting the formation of ethanol by the formation of $NAD^+$ or by the direct detection of the product after analytical separation (CE (capillary electrophoresis), HPLC, and TLC).

The signals are measured by all suitable sensors that can measure the generated signals, such as, for example, a fluorimeter, a spectrophotometer, an amperometer, a pH meter, a thermometer, or a thermographic probe. The idiosyncratic catalytic imprint that is generated is collected by an analyzer that is suitable for the recognition of signals.

Regardless of the implementation of the invention, the signals that are generated after the contact of stage (a) can be captured in stage (b) by using a separation technique such as HPLC.

Advantageously, the substrates are such that the generated signals are of the same type.

They can be measured on the same type of sensor.

The idiosyncratic catalytic imprint that corresponds to the generated signals can be interpreted directly or indirectly after processing raw values. This processing will be considered based on analyzed signals.

The substrates advantageously exhibit the characteristic of reacting over a short reaction time, for example less than 2 hours, preferably less than 20 minutes. This characteristic has the advantage of quickly obtaining the idiosyncratic catalytic imprint of a sample. It also makes possible a study of its evolution over time. This facilitates in particular the analyses of quality control.

The substrates that are used in the process of the invention advantageously each have a specific reactivity for a given type of catalytic activity. They show little or no sensitivity to degradation or to non-specific activities. In addition, when stable substrates are used, they can be preserved during long periods.

The process of the invention makes it possible to follow a sample over time through its idiosyncratic catalytic imprint by using substrates from which several measurements can be carried out.

The visualization of the effect of catalytic activities on a group of substrates can be reproduced.

The described substrates advantageously correspond to those that are described in International Patent Appllication PCT/FR01/01686 and in the article by G. Klein and J. L. Reymond, Helvetica Chimica Acta, Vol. 82, 1999, pages 400–407.

These substrates correspond to formulas (I) to (V) below:

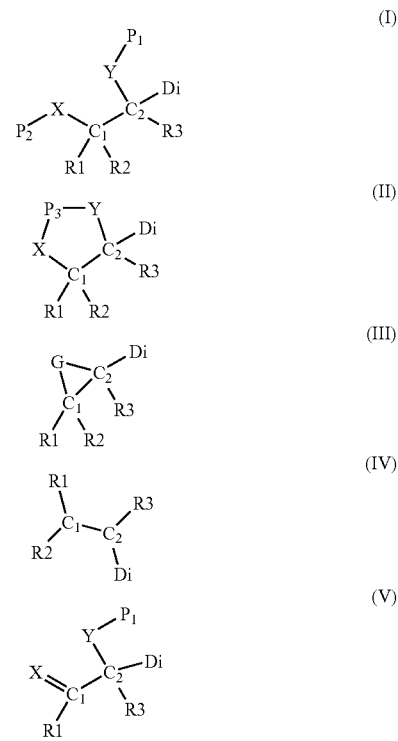

wherein:
the C1–C2 bond is insensitive to a cut by a chemical oxidation reaction.

Di represents the precursor of a detectable product.

X and Y, identical or different, are selected from among an oxygen atom, a sulfur atom, and an amine of formula —$NR_{11}R_{12}$; $R_{11}$ is selected from among: a hydrogen atom, an alkyl group, an aryl group, which may or may not be substituted, and $R_{12}$ is not a hydrogen atom.

$R_1$ to $R_3$, identical or different, are selected from among a hydrogen atom, an alkyl group that may or may not be substituted, or a chemical group as defined above.

$P_1$ and $P_2$, identical or different, are functional groups as defined above, and at most one of groups $P_1$ and $P_2$ is a hydrogen atom.

$P_3$ is selected from among a carbonyl group, a group —$PO_2R_{11}$ or a group $R_{11}PO$—, where $R_{11}$ has the same meaning as above, a group —$SO_2$, a group —$CHOR_{13}$ where $R_{13}$ represents an aryl group, alkyl group or glycosyl group, a group $SiR_{14}R_{15}$, where $R_{14}$ and $R_{15}$, identical or different, represent an aryl group, alkyl group, aryloxy group or alkoxy group and a group $AsO_2H$—.

G is selected from among an oxygen atom, a sulfur atom, an amine group of formula $NR_{13}$ where $R_{13}$ is $R_{11}$ or $R_{12}$, $R_{11}$ and $R_{12}$, having the same meaning as above.

Figure 2:
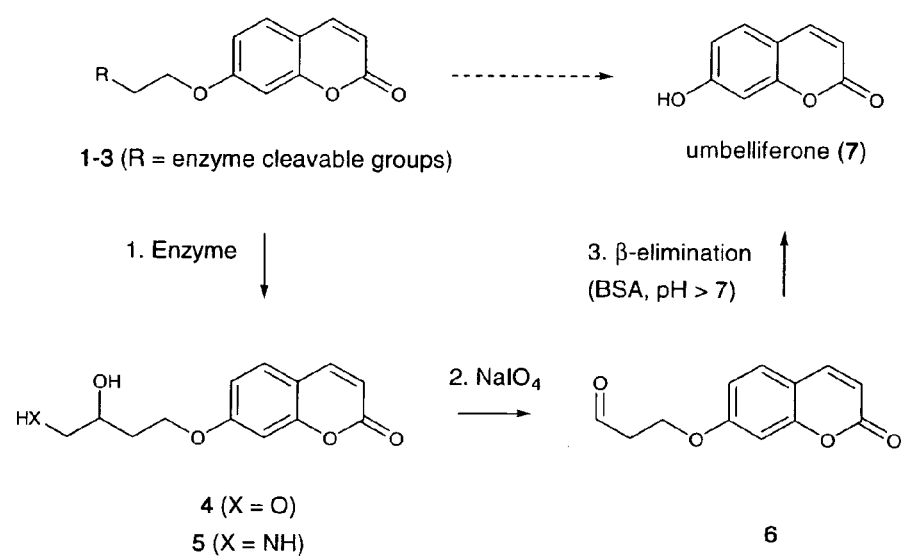
FIG. 2 shows a principle for detection of fluorescent substrates.

These substrates are detected after their chemical transformation by a sample to provide products that will be oxidized chemically to obtain directly or indirectly a detectable compound that corresponds to one or more compounds that can exhibit by themselves or in combination one or more variations of their biophysical properties, biological properties or chemical properties before and after the oxidation stage such as in particular a variation of the spectral type or a variation of solubility. By way of example, FIG. 2 represents a principle for detection of fluorescent substrates.

A second example of useful substrates according to the process of the invention comprises substrates (S) whose transformation into product (P) can be detected by measuring a change of pM resulting from the difference of the chelating power of substrate (S) and product (P) with regard to a metal ion. Such substrates are described in French Patent Application No. 01/05574 and in the articles by Jean-Louis Reymond et al. (G. Klein, D. Kaufmann, S. Schürch and J. L. Reymond, *Chem. Commun.*, 2001, 561–562; G. Klein and J. L. Reymond, *Angew. Chem. [Applied Chemistry]*, 2001,113, No. 9). These substrates make possible the detection of the transformation of a substrate (S) into a product (P) by measuring the change in spectral properties of a chemical detector (L), chelating agent of a metal ion, resulting from exchanges of metal ions according to the following balance:

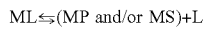

ML ⇌ (MP and/or MS)+L where:

S represents a substrate, which can be any chemical molecule, whose chelating power is different from that of the product that results from the chemical transformation of the substrate. It is a matter in particular of a specific substrate such as entire proteins for the proteases. This substrate may have enantioselective properties. The substrates do not have any structural constraint other than that of having a difference in chelating power with the corresponding products.

P represents the product that is obtained from the chemical transformation of S and that has a chelating power that is different from S. Like the substrates, the products do not have a structural constraint other than that of having a difference of chelating power with the corresponding substrates.

L represents a chemical detector, also designated a "pM sensor," corresponding to any ligand that can chelate the metal ions in solution such that the chelation of the metal by the chemical detector provides a change in pM that can be measured by any suitable method, such as, for example, a change in the spectral property of the detector. The pM sensor has a chelating power such that it can have exchanges of metal ions there between product (P) and ligand (L) or substrate (S) and ligand (L) respectively according to which product (P) or substrate (S) has the strongest chelating power. As indicated above, the chelating power of chemical detector (L) is advantageously greater than that of substrate (S) or of product (P) so as to carry out the method of the invention with small amounts of chemical detectors. Chemical detector (L) may correspond to a derivative of fluorescein or any other fluorescent core that is substituted by a chelating group.

ML represents the metal-ligand complex that has spectral properties that are different from L.

MS represents the metal-substrate complex.

MP represents the metal-product complex.

Said complexes ML, MS and MP do not necessarily have a stoichiometry of 1/1.

These substrates make possible the detection of the transformation of a substrate (S) into a product (P) by measuring the change in spectral properties of a chemical detector (L), chelating agent of a metal ion, resulting from exchanges of metal ions:

Between product (P) and chemical detector (L) when product (P) has a chelating power that is higher than that of substrate (S), or Between substrate (S) and chemical detector (L), when substrate (S) has a chelating power that is higher than that of product (P).

A combination of different substrates can be used to carry out the idiosyncratic catalytic imprints.

The invention also has as its object a group of substrates that make it possible to generate the idiosyncratic catalytic imprint according to the process of the invention.

In an implementation of the invention, substrates will be selected that have different functional groups or different chemical groups or a combination of these two possibilities, in particular substrates that have identical functional groups and different chemical groups.

In another implementation, the substrates will be identical. The contact of substrates with the sample will then be made under different reaction conditions. The reaction conditions, by way of nonlimiting example, are in terms of the pH, the temperature, the incubation period, the concentration of substrate or a sample amount or a mixture of the latter. These conditions can also correspond to other parameters that can be taken both individually or in combination. These conditions can also correspond to the addition of one or more additional reagents.

The substrates can also correspond to a combination of different and identical substrates.

In a particular embodiment of the invention, the idiosyncratic catalytic imprint of a sample can be carried out by using substrates that may turn out to be different among classes by at least one class of catalytic activity.

By way of example, the substrates such as epoxide, ester, carbonate, amide, cyano, lactam, carbamate, glycoside, alkyl halide, monoester and diester phosphate, enol ether and alkyl ether can make it possible to develop the hydrolasic idiosyncratic catalytic imprint of a sample. Likewise, the substrates such as ethanol, methanol, isopropanol, butanol, glycerol, ethylene glycol, lactic acid, malic acid, citric acid, formic acid, acetic acid, propionic acid, benzoic acid, benzaldehyde, acetaldehyde, and propionaldehyde can make it possible to develop a dehydrogenasic idiosyncratic catalytic imprint of a sample.

The number of substrates is advantageously at most 1000. It is generally on the order of 1 to 200.

The substrates that are used in the process of the invention can be ordered on the same support, such as, for example, on a microtitration plate or a microsystem. This support that has substrates can constitute a system that is used to generate an idiosyncratic catalytic imprint according to the process of the invention. The capture of signals will be carried out in an ordered way thanks to the ordered arrangement of substrates on the support.

The substrates can also be mixed, and in this case, the capture of the signals will be carried out in an ordered way, for example, thanks to a previous calibration.

In an implementation, the signals can be captured in an ordered way by using a separation technique such as HPLC.

The reaction of the substrates with the sample can be followed in real time or at the end point.

The idiosyncratic catalytic imprints that are obtained can be stored so as to create databases of sample imprints.

The idiosyncratic catalytic imprint of a sample can correspond to the combination of several imprints that are obtained according to different implementations and over time.

After collecting idiosyncratic catalytic imprints of signals that are generated by a sample, the process of the invention can also comprise an analysis of the idiosyncratic catalytic imprint. This analysis makes it possible to characterize or to carry out a follow-up of the evolution of the sample. It is not necessary to know exactly all the activities to carry out this analysis.

The signal is based on the modification that is carried out on the activity. Thus, in a sample, catalytic activities that belong to the same class will be able to react on the same substrates with a different reaction speed. The generated signal will be different.

The imprint of a sample is likely to change, for example, because the sample was put into the presence of contaminants or because the sample becomes degraded or is altered over time. For the follow-up of the evolution of the sample, such as, for example, quality control, it is possible to consider the result that is obtained in comparing it to an imprint that forms part of a database or to an imprint that is carried out before or after the analyzed sample.

The idiosyncratic catalytic imprint that is obtained can be superposed on another imprint that is obtained by way of example:

With the same group of substrates in the presence of a mixture of samples or a reference sample.

With the same sample but with a group of different substrates.

With the same group of substrates developed with the same sample at a different time.

With the same group of substrates developed with the same sample taken at a different time.

With the same group of substrates developed under different reaction conditions.

This comparison of idiosyncratic catalytic imprints can be carried out by all techniques, in particular:

By visual comparison of catalytic imprints for modification or generated signals that are obtained.

By computer graphic analysis.

The modification of an idiosyncratic catalytic imprint of a sample is the indicator of a variation or an appearance or a disappearance of one or more catalytic activities.

The use of the process of the invention and the superposition of imprints is entirely suitable for the follow-up of processes or products using catalytic activities to perform in particular quality control.

The process of the invention is also noteworthy in that it can be automated. Actually, such an automation comprises optionally computer processing transformation results of substrates to obtain the idiosyncratic catalytic digital imprint that is characteristic of signals and interpretating the idiosyncratic imprint to characterize the sample.

By way of example of such a computer processing, it is possible to cite most particularly the one that relates to the combination of several imprints of which the processing generates a new graphic imprint in colors that makes it possible to visualize accumulated characteristics of a sample. This method for visualizing results makes it possible to accumulate at least two measurements (two signals) to create new data represented in the form of a specific value. This value provides data on a characteristic of the sample of interest. In Example 4 below, the value that is obtained is translated into a specific color.

The processing of the imprints can include a color display of the new imprint of the type that is based on the RGB (red, green, blue) system.

The invention also has as its object a system for the implementation of the process that is described above, comprising a mixture of substrates and one or more of the following accessories:

A device for controlling the contact of the sample with at least one substrate;

Sensors for separating and measuring the signals that are generated starting from the transformation of the substrates by the sample;

A first analyzer that makes it possible to generate the idiosyncratic catalytic imprint of a sample;

A memory that makes it possible to store in a database the original idiosyncratic catalytic imprints; and/or A second analyzer that makes possible the superposition between the idiosyncratic catalytic imprint that is newly obtained and the set of imprints stored in memory.

The invention also has as its object a system that comprises a support on which are ordered several substrates as defined above, identical or different, making it possible to implement the process of the invention. This system can comprise, in addition to the group of substrates, one or more of the following accessories:

A device that is used to control the contact of the sample with at least one substrate.

Sensors for measuring the signals generated from the transformation of substrates by the sample. These sensors can correspond by way of nonlimiting example to a fluorimeter, a spectrophotometer, an amperometer, and a pH meter.

An analyzer that makes it possible to generate the idiosyncratic catalytic imprint of a sample. The imprint will be stored, for example, in the form of a series of grayscale bits or by using the RGB system.

A memory that makes it possible to store in a database the original idiosyncratic catalytic imprints.

An analyzer that makes possible the superposition between the idiosyncratic catalytic imprint that is newly obtained and the set of imprints stored in memory. This analyzer will be able to carry out statistical tests that are known to one skilled in the art, making it possible to carry out analyses of differences and similarities between the imprint, newly obtained, and the set of imprints stored in memory.

These statistical tests may involve, for example, tests of discrepancy or correlation.

The system of the invention can be used to carry out the follow-up of the evolution of a sample.

The invention then also relates to the use of a system as defined above to carry out the follow-up of the evolution of a sample, wherein:

At least one sample is brought into contact with a group of substrates that are ordered on said system, each comprising at least one functional group that is sensitive to the presence of catalytic activity of the sample;

The generated signals that result from said contact of substrates with the catalytic activity of a sample are captured; and/or The imprint for a sample is compared to another established imprint.

The system of the invention can be used to carry out the follow-up of the evolution of a sample. The invention then also relates to the use of a system as defined above to carry out the follow-up of the evolution of a sample wherein:

At least one sample is brought into contact with a group of substrates in the form of a mixture, each comprising at least one functional group that is sensitive to the presence of catalytic activity of the sample;

In an ordered way, the generated signals that result from said contact of the substrates with the catalytic activity of a sample are captured by using a separation technique such as HPLC; and/or The imprint for a sample is compared to another established imprint.

Other advantages and characteristics of the invention will come out in the following examples. These examples show that the process of the invention makes it possible to obtain the idiosyncratic imprints of a sample.

The embodiment of these examples can be easily applied to any type of sample.

With regard to the Figures, FIG. 1 shows examples of formulas of fluorogenic substrates (FIG. 1a), and chromogenic substrates (FIG. 1b) that are useful according to the invention.

FIG. 2 shows a principle for detection of fluorescent substrates.

Figure 3:
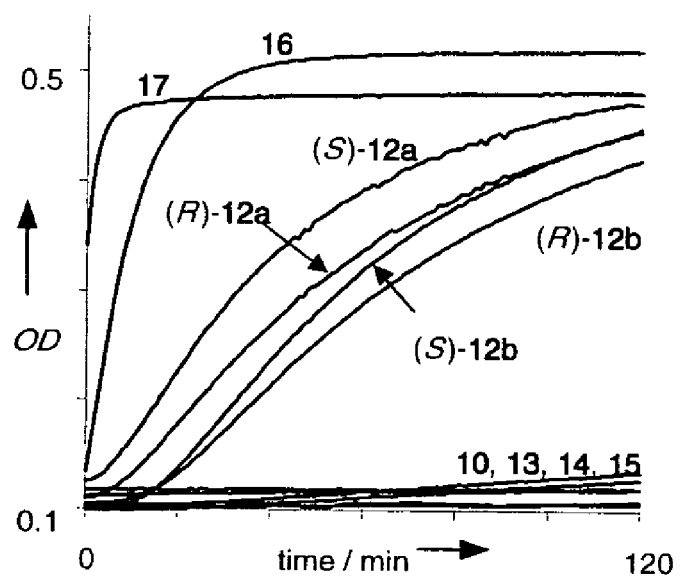
FIG. 3 shows kinetics of an absorbance signal (OD, with $\lambda=405$ nm) for idiosyncratic catalytic imprint of signals that are generated by a sample with the grid of chromogenic substrates.

FIG. 3 shows the kinetics of the absorbance signal (OD, with λ=405 nm) for the idiosyncratic catalytic imprint of signals that are generated by a sample with the grid of chromogenic substrates.

Figure 4:
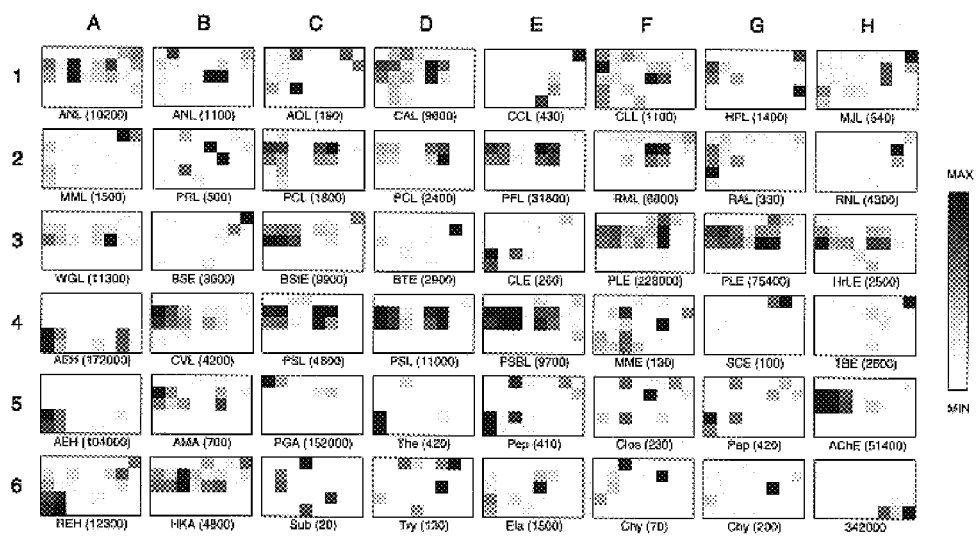
FIG. 4 shows idiosyncratic catalytic imprints that are obtained with fluorescent substrates.
Figure 4B:
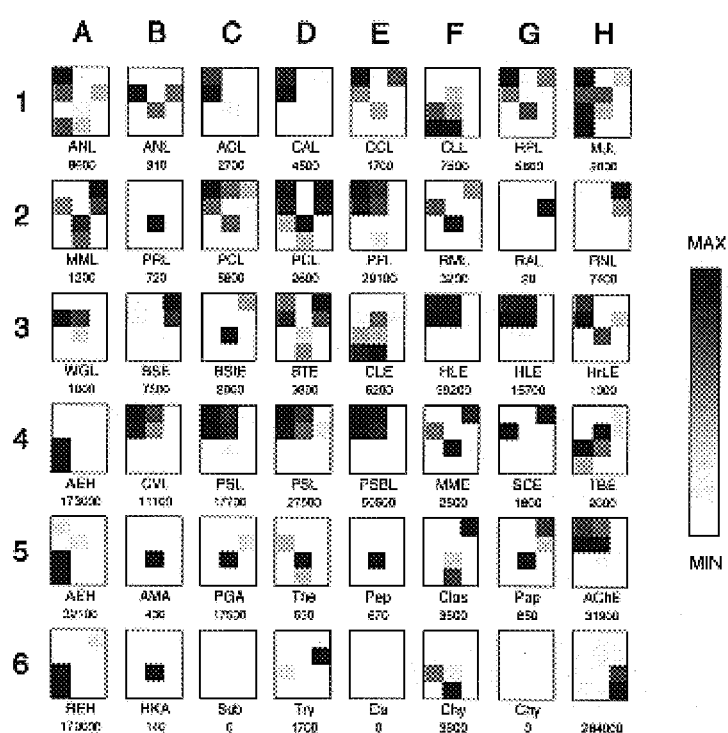
FIG. 4b shows idiosyncratic catalytic imprints that are obtained with chromogenic substrates.

FIG. 4 shows the idiosyncratic catalytic imprints that are obtained with fluorescent substrates. The distribution of the substrates was provided in FIG. 1a. The different samples that are tested by the imprint are indicated in Table 1 below. FIG. 4b shows the idiosyncratic catalytic imprints that are obtained with chromogenic substrates. The distribution of substrates was provided in FIG. 1b. The different samples that are tested by imprint are indicated in Table 1 below.

TABLE 1

| | |
|---|---|
| 1 | A = *Aspergillus niger* lipase (ANL), B = *Aspergillus niger* lipase (ANL) 1 U/mg, C = *Aspergillus oryzae* lipase (AOL), D = *Candida antarctica* lipase (CAL), E = *Candida cylindracea* lipase (CCL), F = *Candida lipolytica* lipase (CLL), G = hog pancreatic lipase (HPL), H = *Mucor javanicus* lipase (MJL) |
| 2 | A = *Mucor miehei* lipase (MML), B = *Penicillium roqueforti* lipase (PRL), C = *Pseudomonas cepacia* lipase (PCL) 40 U/mg, D = *Pseudomonas cepacia* lipase (PCL) 50 U/mg, E = *Pseudomonas fluorescens* lipase (PFL), F = *Rhizomucor miehei* lipase (RML), G = *Rhizopus arrhizus* lipase (RAL), H = *Rhizopus niveus* lipase (RNL) |
| 3 | A = wheat germ lipase (WGL), B = *Bacillus* sp. esterase (BSE), C = *Bacillus stearothermophilus* esterase (BStE), D = *Bacillus thermoglucosidasius* esterase (BTE), E = *Candida lipolytica* esterase (CLE), F = hog liver esterase (HLE) 100 µg/ml, G = hog liver esterase (HLE) 10 µg/ml, H = horse liver esterase (HrLE) |
| 4 | A = *Aspergillus niger* epoxide hydrolase (AEH) 100 µg/ml, B = *Chromobacterium viscosum* lipoprotein lipase (CVL), C = *Pseudomonas* sp. lipoprotein lipase (PSL) 1500 U/mg, D = *Pseudomonas* sp. lipoprotein lipase (PSL) 50000 U/mg, E = *Pseudomonas* sp. Type B lipoprotein lipase (PSBL), F = *Mucor miehei* esterase (MME), G = *Saccharomyces cerevisiae* esterase (SCE), H = *Thermoanaerobium brockii* esterase (TBE) |
| 5 | A = *Aspergillus niger* epoxide hydrolase (AEH) 10 µg/ml, B = Aspergillus melleus acylase I (AMA), C = *Escherichia coli* penicillin G acylase (PGA), D = *Bacillus thermoproteolyticus* thermolysin (The), E = porcine stomach mucosa pepsin (Pep), F = *Clostridium histolyticum* clostripain (Clos), G = Papaya latex papain (Pap), H = *Electrophorus electricus* acetylcholine esterase (AChE) |

TABLE 1-continued

| | |
|---|---|
| 6 | A = *Rhodotorula glutinis* epoxide hydrolase (REH), E = hog kidney acylase I (HKA), C = *Bacillus licheniformis* subtilisin (Sub), D = hog pancreas trypsin (Try), E = porcine pancreatic elastase (Ela), F = bovine pancreatic α-chymotrypsin (Chy) 37 U/mg, G = bovine pancreatic α-chymotrypsin (Chy) 70 U/mg, H = blank |

Figure 5:
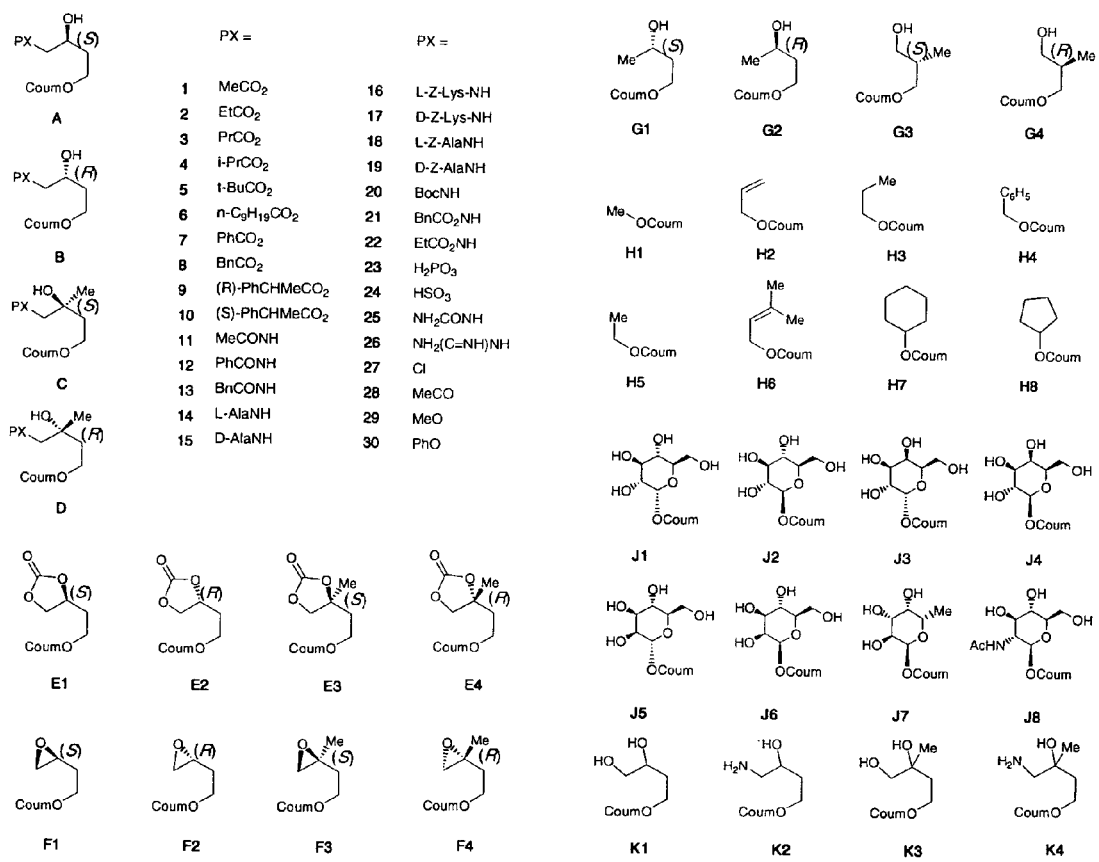
FIG. 5 shows a list of tested substrates.

FIG. 5 shows the list of tested substrates.

FIG. 6 shows stages of processing values to form a color imprint of a catalytic activity. In particular, FIG. 6A shows processing of data to obtain relative values. FIG. 6B shows backup up values in a comma separated value(s) (CSV) file format. FIG. 6C shows creation of a portable pixmap (PPM) file format. And FIG. 6D shows an image of an imprint (in a bitmap (BMP) file).

Figure 7:
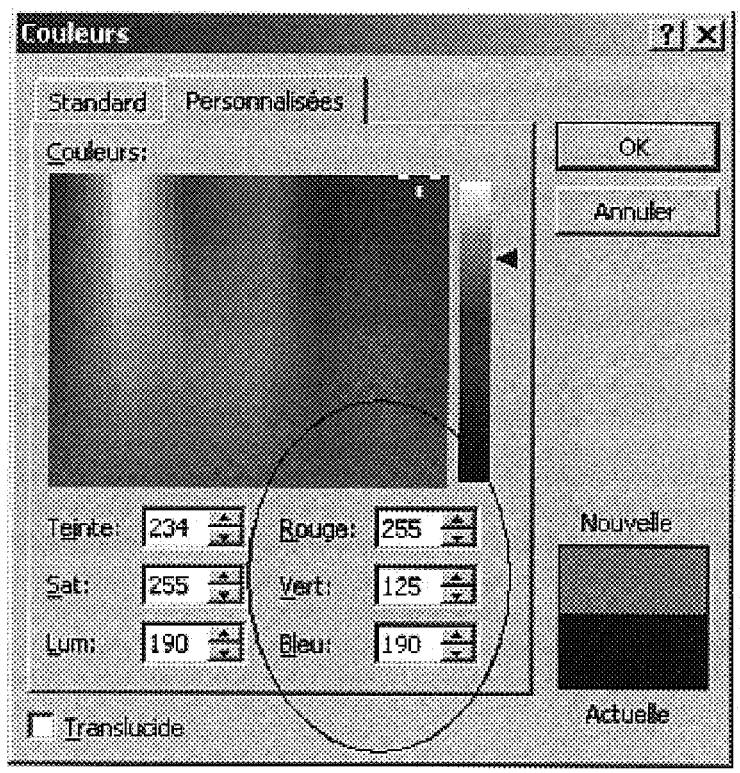
FIG. 7 shows an example of the RGB (Red, Green, Blue) system for color coding.

FIG. 7 shows an example of the RGB (Red, Green, Blue) system for color coding (available in each program of the Microsoft Office Pack).

Figure 8:
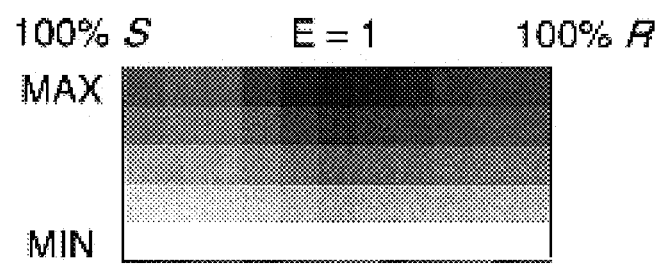
FIG. 8 shows a key of colors and the relationship of tint with selectivity and intensity with reaction speed.

FIG. 8 shows the key of the colors that are obtained according to Example 3 and indicates the relationship of the tint with the selectivity and the intensity with the reaction speed.

Figure 9:
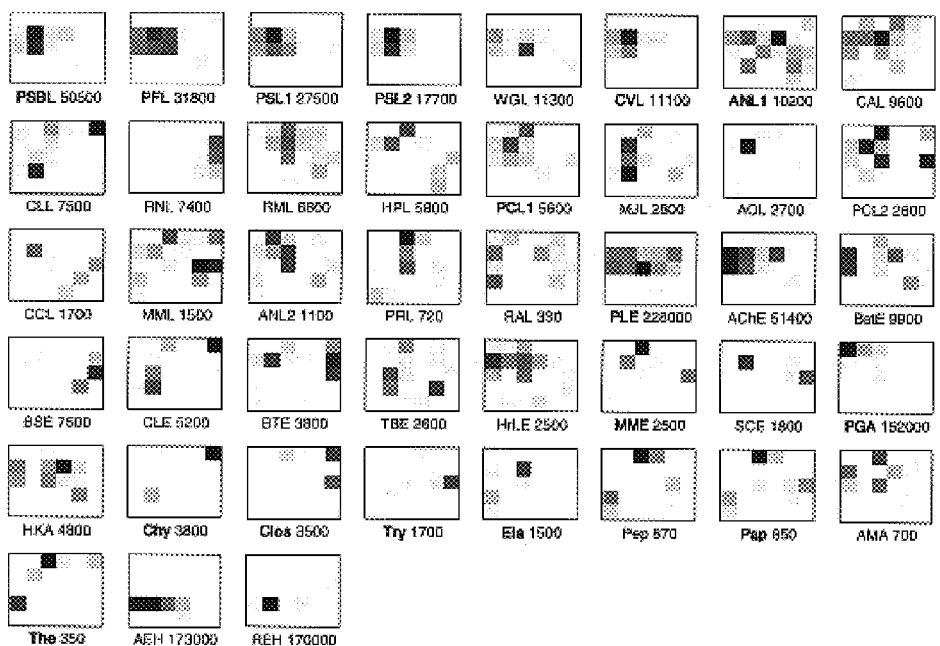
FIG. 9 shows imprints.

FIG. 9 shows the imprints that are obtained in Example 5 by combination of the results that are cited in Example 1.

Figure 10:
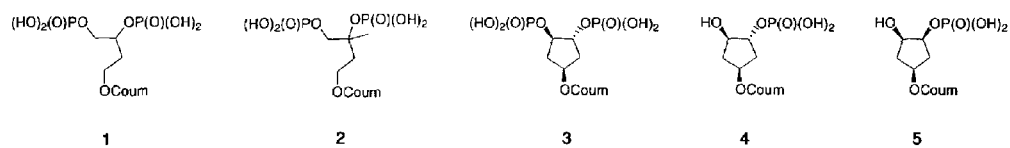
FIG. 10 shows different fluorogenic and chromogenic substrates.

FIG. 10 shows different fluorogenic and chromogenic substrates.

FIG. 11 shows the idiosyncratic imprints that are obtained in Example 6, as well as the maximum conversion percentages.

Figure 12:
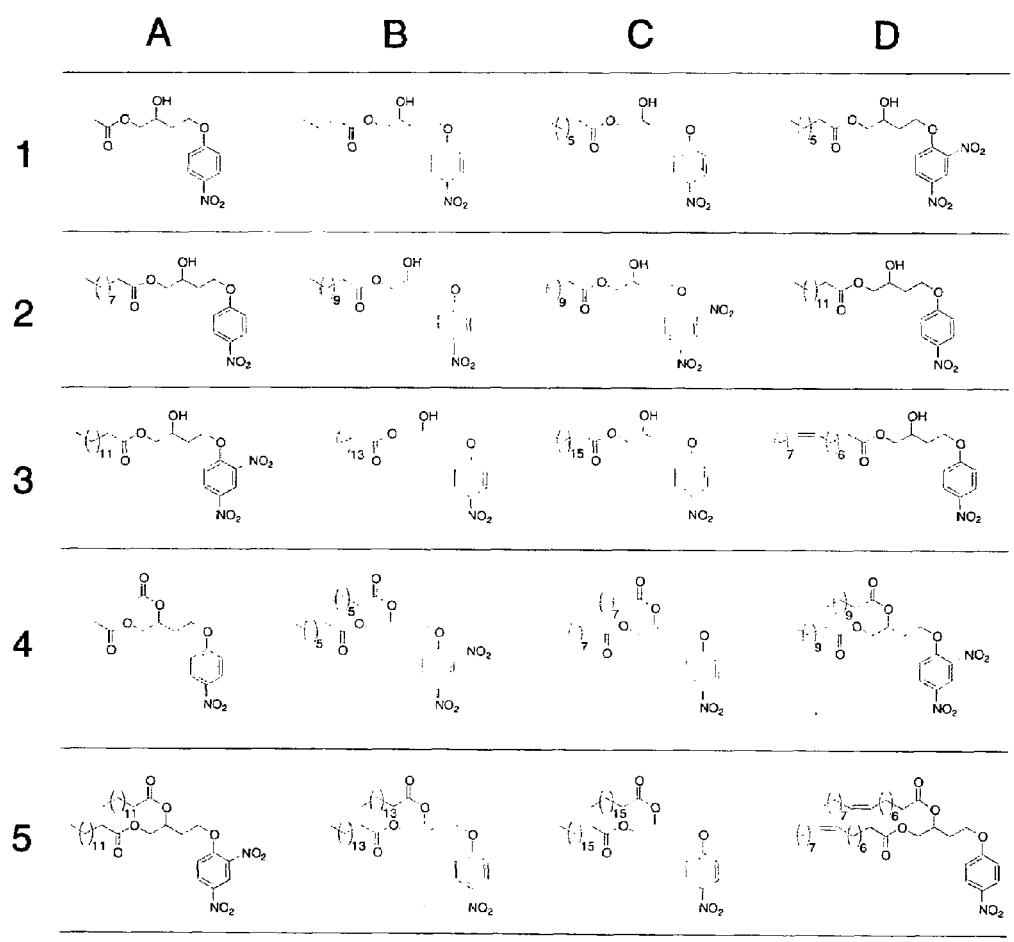
FIG. 12 shows a series of chromophoric substrates.

FIG. 12 shows a series of chromophoric substrates that are used in Example 7 under experimental conditions for capturing signals that are identical to those described in Example 1.

Figure 13:
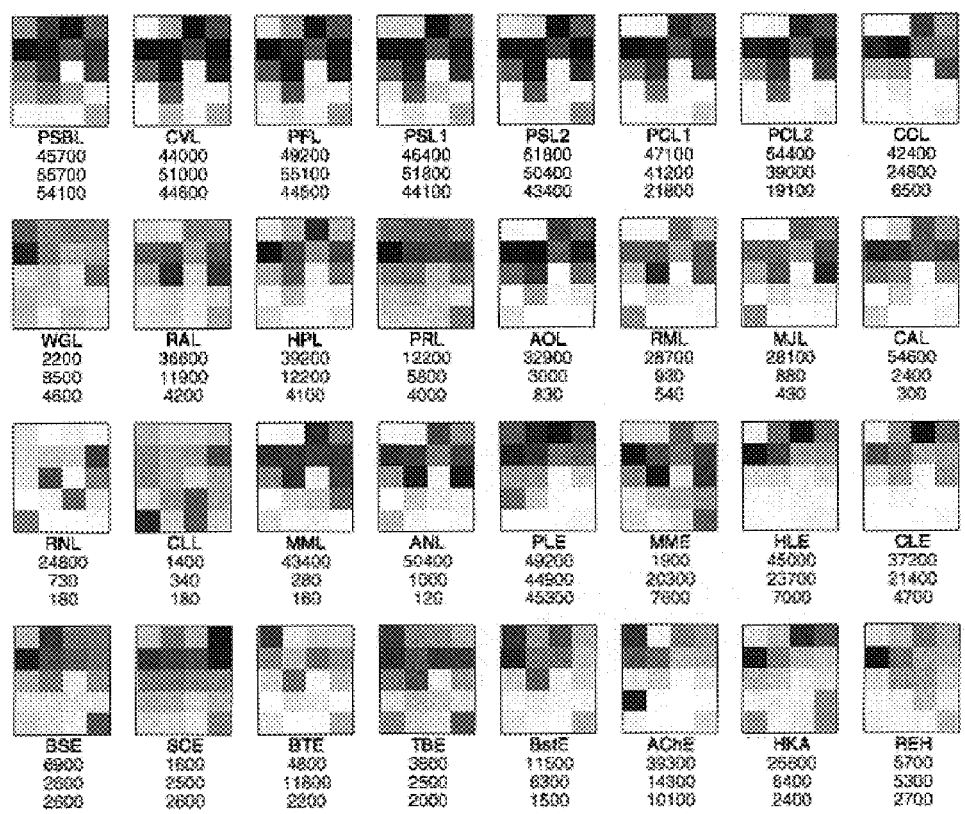
FIG. 13 shows idiosyncratic imprints of catalytic activity.

FIG. 13 shows the idiosyncratic imprints of the catalytic activity based on the dilution of the catalyst obtained in Example 7.

Figure 14:
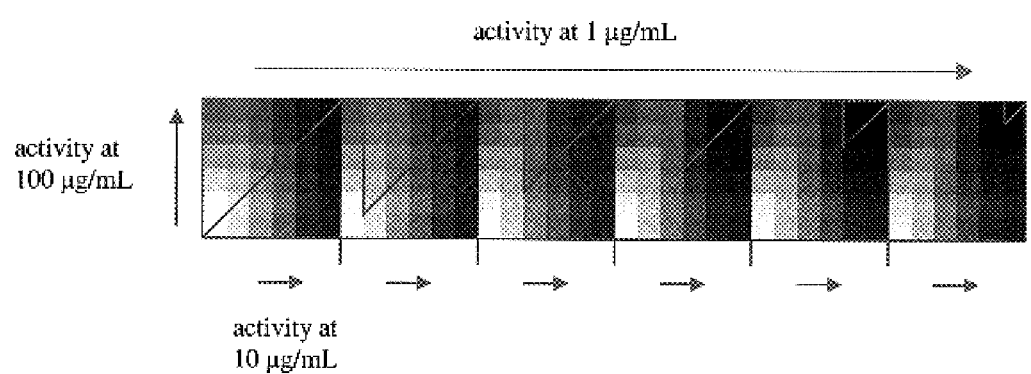
FIG. 14 shows a color coding for substrates.

FIG. 14 shows the color code that is established according to Example 4 for each substrate of Example 7.

Figure 15:
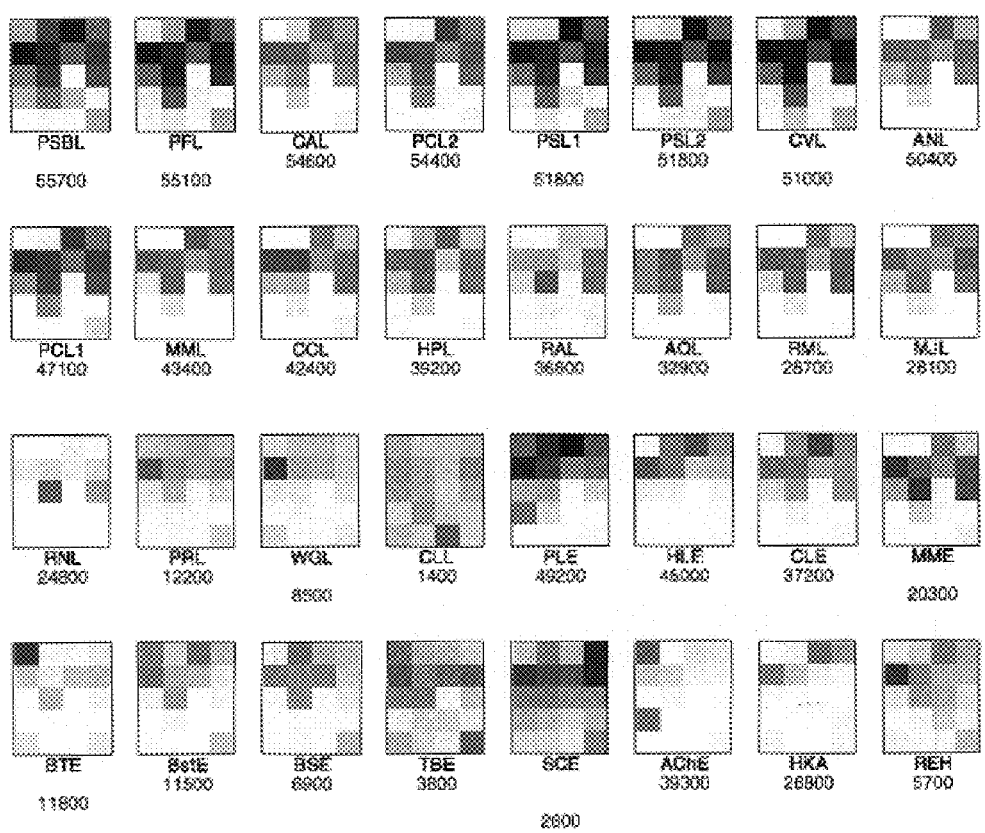
FIG. 15 shows visualization of catalytic activity of a sample.

FIG. 15 shows the visualization of the catalytic activity of the sample of Example 7 based on its dilution, by taking into account only the maximum speed that is obtained over all of the measurements taken with this sample.

Figure 16:
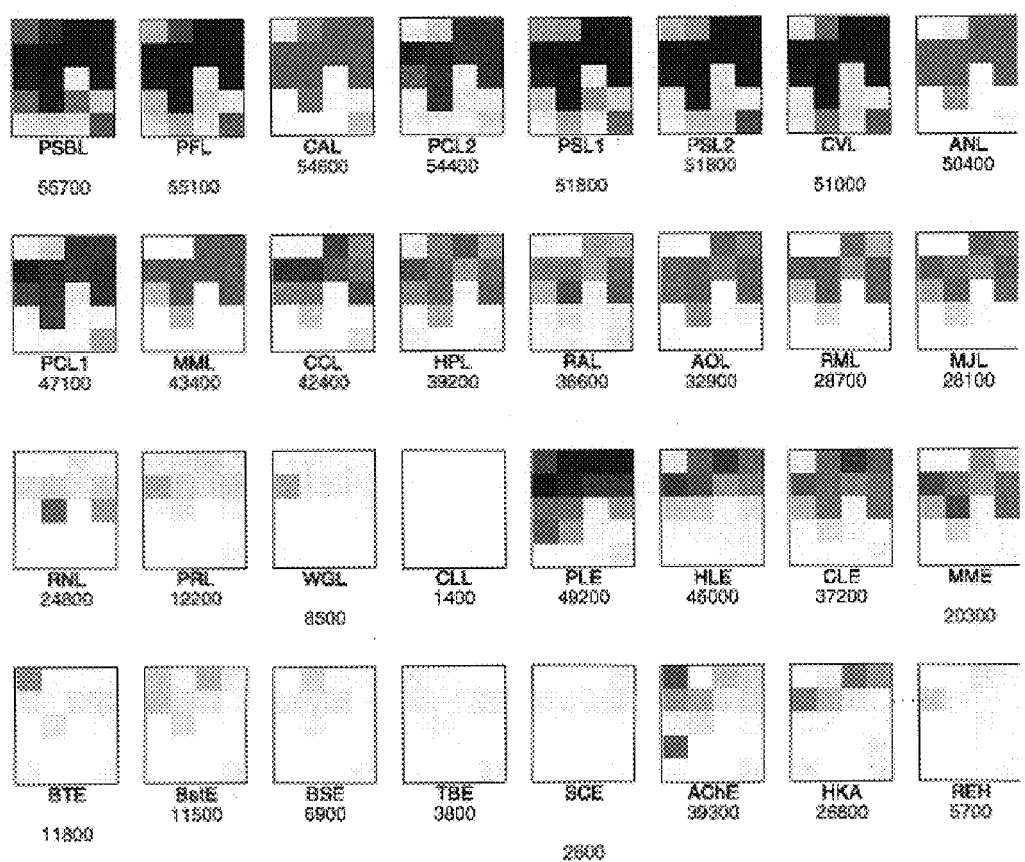
FIG. 16 shows truncated visualization of catalytic activity of a sample.

FIG. 16 shows the same processing as in FIG. 15 of Example 7 but by truncating the results that are obtained for the better substrates by omitting the values that are more than 25000 pM/s, which are related to the color black.

FIG. 17 shows a series of 1,2-diols of various structures that can be analyzed by HPLC.

Figure 18:
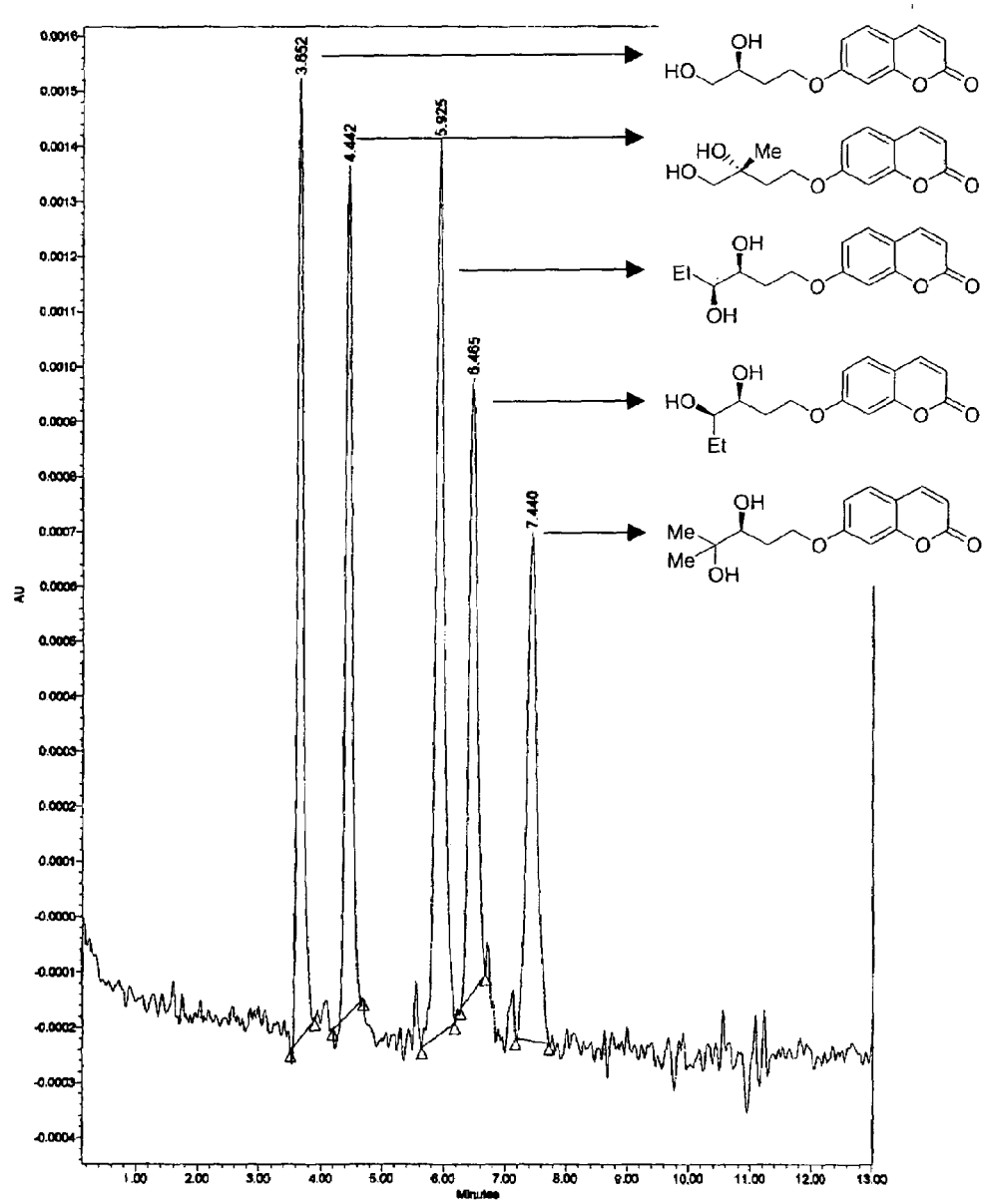
FIG. 18 shows an example of an HPLC trace of a series of 1,2-diols of diverse structure.

FIG. 18 shows an example of the HPLC trace of a series of 1,2-diols of diverse structure.

Figure 19:
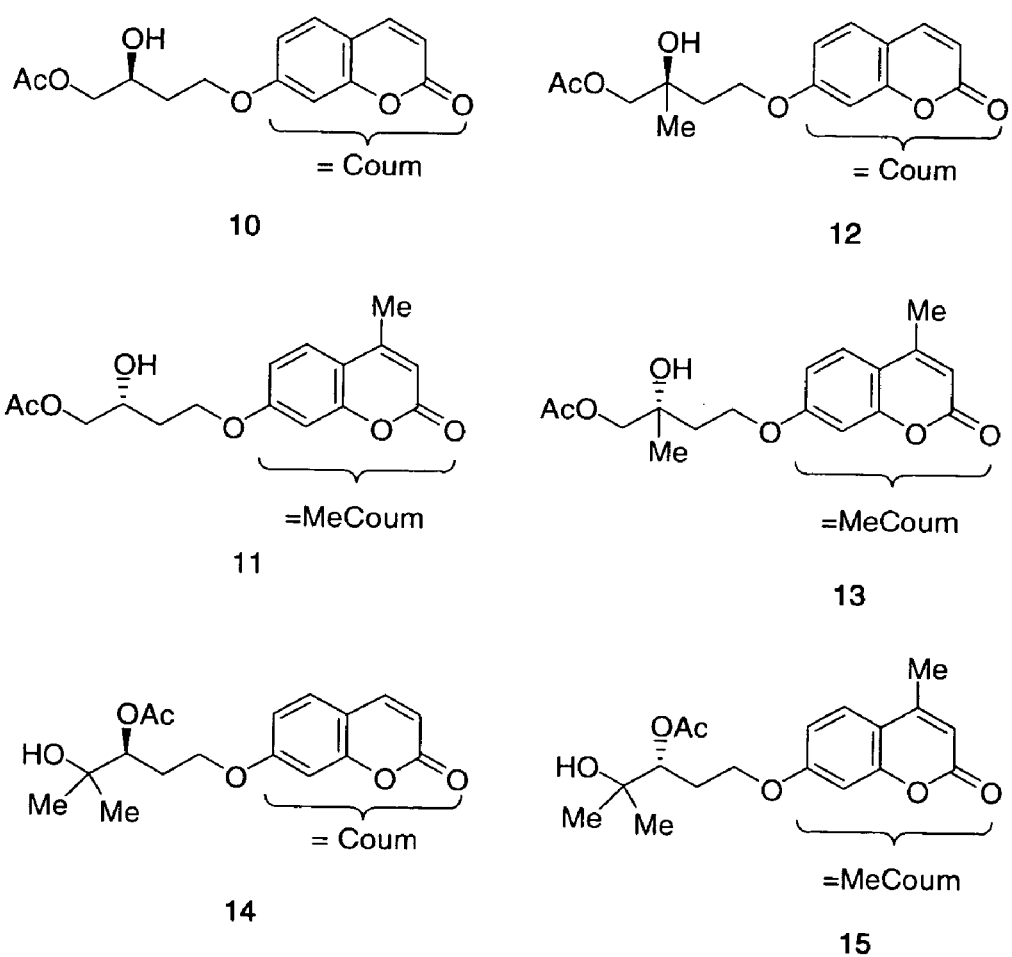
FIG. 19 shows a series of pseudo-enantiomeric acetates.

FIG. 19 shows a series of pseudo-enantiomeric acetates that can be mixed by pairs so as to carry out a simple imprint of esterase activity on acetates.

Figure 20:
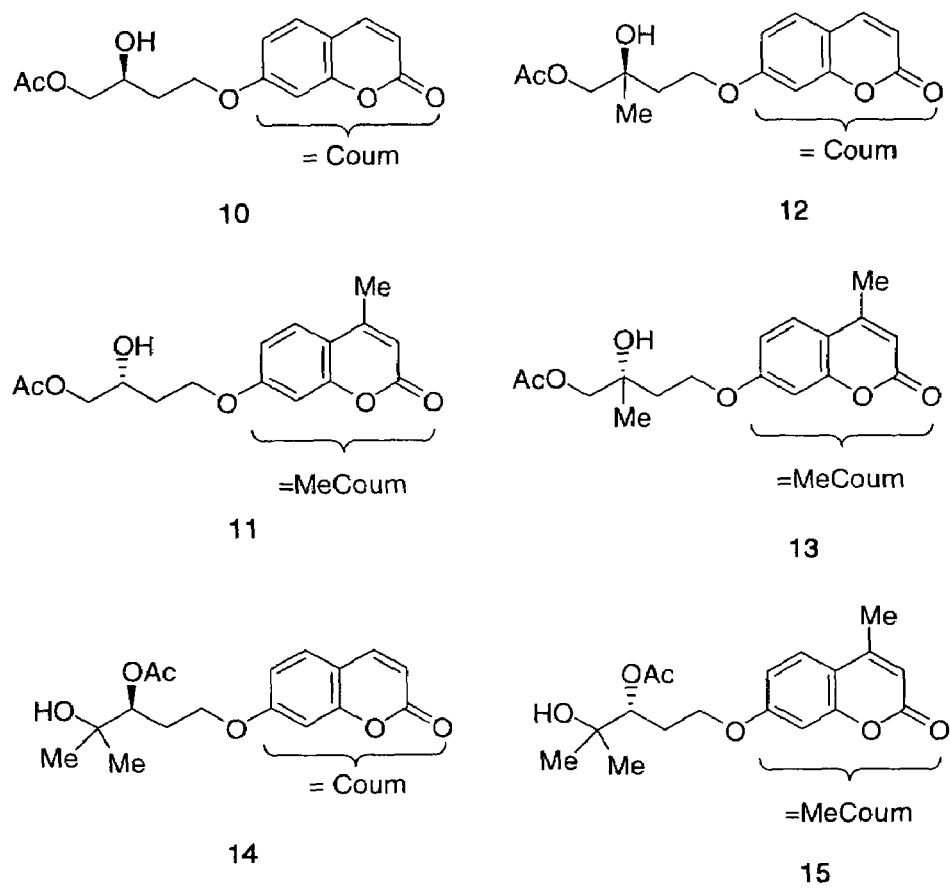
FIG. 20 shows a series of 10 ester/carbonate substrates that can be used in an equimolar mixture to measure the esterase imprint of a sample.

FIG. 20 shows a series of 10 ester/carbonate substrates that can be used in an equimolar mixture to measure the esterase imprint of a sample.

FIG. 21 shows a series of products exhibiting a variety of functional groups for an analysis by HPLC of a mixture of the latter.

Figure 22:
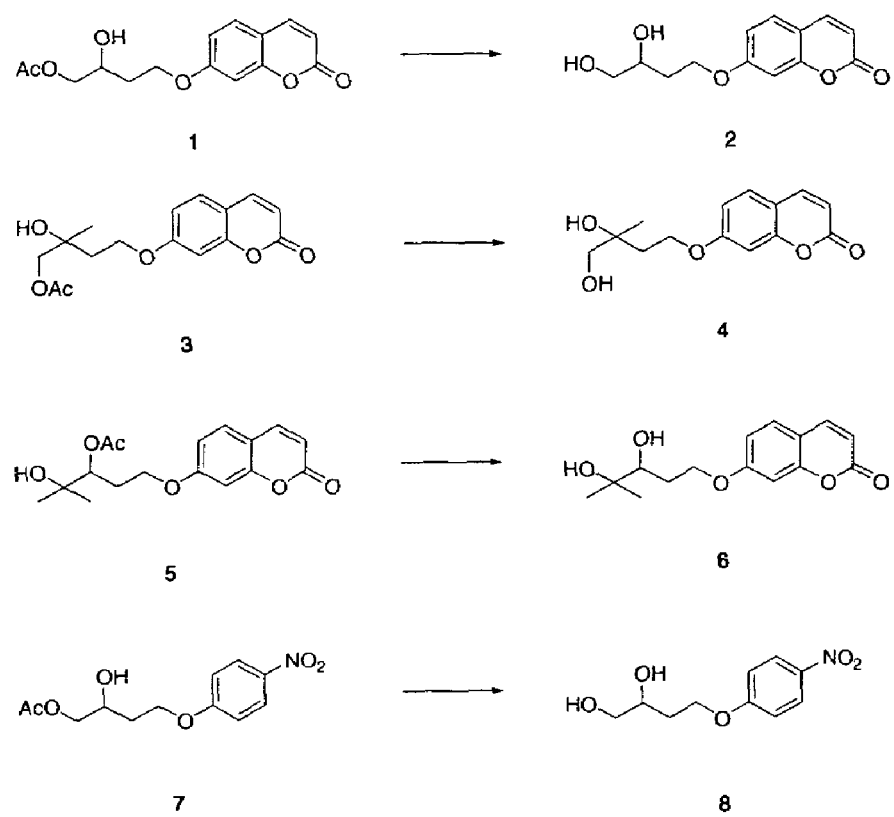
FIG. 22 shows structures of four ester substrates used to generate an idiosyncratic catalytic activity imprint of lipase-esterase-type enzymes.

FIG. 22 shows the structure of the four ester substrates that are used to generate the idiosyncratic catalytic activity imprint of lipase-/esterase-type enzymes.

Figure 23:
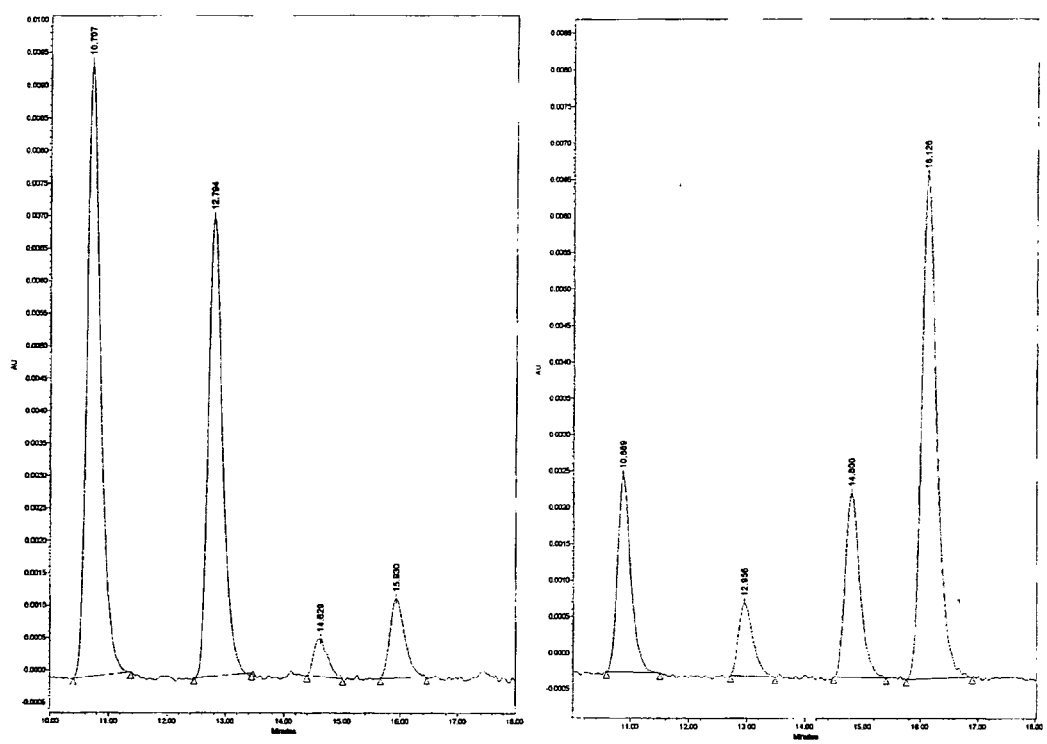
FIG. 23 shows HPLC traces that provide an idiosyncratic imprint of *Mucor Miehei* esterase (left) and *Pseudomonas Fluorescens* lipase (right).

FIG. 23 shows the HPLC traces (UV 295 mm) that provide the idiosyncratic imprint of the *Mucor Miehei* esterase (left) and the *Pseudomonas Fluorescens* lipase (right).

FIG. 24 shows the idiosyncratic imprints of the *Mucor Miehei* esterase (1) and the *Pseudomonas Fluorescens* lipase (2). Each square of the grid corresponds to the surface area of the peak of one of the four products that are obtained after enzymatic activity.

EXAMPLES

Example 1

Idiosyncratic Catalytic Imprints of Samples.

(1) The various fluorescent and chromogenic substrates are placed in the wells of microtitration plates respectively according to the arrangement of FIGS. 1a and 1b in the form of 5 microliters of a stock solution with 2 mmol in a 50/50 DMF/water mixture. The grid comprises solutions of reference products that will be used as a positive control in the measurement.

(2) A solution of a predeliluted sample is then added into each well in a buffer that contains the developer agent (1 mmol of $NaIO_4$, 2 mg/ml of BSA), and the reaction is followed based on time for 2 hours. The list of tested samples is shown in Table 1. Only the data of the first 30 minutes are necessary for the subsequent calculation of the generated signals to carry out the corresponding idiosyncratic catalytic imprints.

(3) The imprints are obtained in the following manner:
(a) Conversion of the fluorescence or absorbence data at 405 nm into an umbelliferone or nitrophenol concentration according to the calibrating curves. A typical reaction imprint is shown by way of example in FIG. 3. Conditions: 0.1 mg/ml of an enzymatic sample, 100 μm of substrate, 20 mmol of aqueous borate, pH 8.8, 2.5% with regard to DMF, 26° C., 2 mg.ml$^{-1}$ of BSA, 1 mmol of $NaIO_4$. The speeds that are determined from these curves are as follows: 17 209,300 pM.s$^{-1}$, 16 130,800 pM.s$^{-1}$, (S)-12a 31,800 pM.s$^{-1}$, (S)-12b 25,500 pM.s$^{-1}$, (R)-12a 25,000 pM.s$^{-1}$, (R)-12b 22,000 pM.s$^{-1}$, 15 4,000 pM.s$^{-1}$, (R)-10 2,600 pM.s$^{-1}$, (S)-10 2,300 pM.s$^{-1}$, 14 1,600 pM.s$^{-1}$, (S)-13 1,400 pM.s$^{-1}$, (R)-13 1,300 pM.s$^{-1}$.

(b) Determination of apparent maximum speeds starting from the apparent maximum slope in the speed imprint, which is always located before 30 minutes of reaction (FIG. 3).

(c) Subtraction of recorded speeds for the reference measurement without a sample under the same conditions.

(d) Division of all the speeds by the maximum speed observed in the grid for a given sample.

(e) Coloration of the case corresponding to the grayscale substrate in proportion to the relative speed. 0=white. Maximum=black.

The display of the analyzed imprint, which is necessary for visual analysis, can advantageously take the form of a square or rectangular grid where each square of the grid is tinted in grayscale in proportion to the value that is attributed to a given substrate of the series, varying from white (no activity) to black (maximum activity).

The idiosyncratic catalytic imprint of the generated signals is then displayed as well as the value of the apparent maximum speed in pM/s.

We verified that these measurements can be reproduced, namely that the same sample provides the same idiosyncratic catalytic imprint when the measurement is repeated under the same conditions. 0.1 mg/ml of sample, 2 mg/ml of BSA (bovine serum albumin), 20 mmol of borate buffer, pH 8.8, 0.1 mmol of each substrate, 1 mmol of $NaIO_4$, incubation 26° C.

For FIGS. 4a and 4b, 47 samples provided in Table 1 above were tested.

The corresponding idiosyncratic imprints were obtained (FIGS. 4a and 4b). They illustrate the individual capacity of each sample to react with a group of substrates.

Example 2

Combination of Substrates that can be Used to Generate the Idiosyncratic Catalytic Imprint of a Sample.

The 148 substrates and 4 control substrates, whose formulas are provided in FIG. 5, were used.

All of the substrates are tested at the concentration of 0.1 mmol at pH 7.4, under two types of conditions:
1) In direct time: sample (0.1 mg/ml), BSA (2 mg/ml), an aqueous inorganic buffer (phosphate, borate, ammonium carbonate) (10–100 mmol), with 7<pH<11. Temperature between 15 and 45° C.
2) At the end point: a) incubation of the sample (0.1 mg/ml) at a given pH/temperature in an inorganic buffer; b) addition of stabilizing buffer to obtain a final pH of between 7 and 9, BSA (2 mg/ml), then recording of the signal either directly or after 20 minutes.

Substrates A–F and controls K: addition of NaIO4 (1 mmol).

Substrates G: Addition of NAD* (1 mmol) and NADP$^+$ (1 mmol).

The signals that are generated after the contact of this group of substrates with a sample will be fluorescent.

These various substrates make it possible to develop the following enzyme classes:
Lipases, esterases, proteases, and amidases: A1–A22, B1–B22, C1–C22, D1–D22, E1–E4
Phosphatases: A23–D23
Sulfatases: A24–D24
Ureases: A25–D25
Argininases: A26–D26
Dehalogenases: A27–D27
Aldolases: A28–D28 without $NaIO_4$
Bayer villigerases: A28–D28 with lipase and $NaIO_4$
Ether hydrolases: A29–D29, A30–D30
Epoxide hydrolases: F1–F4
Alcohol dehydrogenases: G1–G4 without $NaIO_4$ with NAD$^+$/NADP$^+$
Hydroxylases: H1–H8 without $NaIO_4$
Glycosidases: J1–J8 without $NaIO_4$ In another implementation, the same grid of substrates with para-nitrophenol replacing coumarin (Coum) as a leaving group will be produced. The signals that are measured after the contact of the substrates with the sample will be chromogenic.

Example 3

Idiosyncratic Imprint by Using Substrates that Require the Presence of a Sensor.

The idiosyncratic imprint of a sample can be carried out by a grid of non-chromogenic or non-fluorogenic substrates if the reaction can be followed indirectly, for example with a sensor, such as a thermographic probe, or a pH or pM sensor. By way of example, a grid that consists of esters will be used to obtain the imprint of samples of lipases and esterases by using a pH indicator for the measurement. A series of amino acid derivatives such as the N-acyl amino acids (20 natural L-N-acetyl amino acids +20 corresponding D-N-acetyl amino acids) will advantageously be used to determine sample idiosyncrasy containing acylases by following the reaction with the help of a pM sensor.

Example 4

Generation of an Imprint From Several Imprints and its Graphic Display in Color.

Examples 5, 6 and 7 relate to the combination of several imprints whose processing generates a new graphic imprint in colors making it possible to visualize accumulated characteristics of a sample. This method for visualizing results making it possible to accumulate at least two measurement (two signals) to create new data represented in the form of a specific value. This value provides the information on a characteristic of the sample of interest. In the examples described, the value that is obtained is translated into a specific color.

It thus is possible to assess the selectivity of a sample including its, for example, stereoselectivity, enantioselectivity, activity based on pH, and/or activity based on the concentration of the sample. The processing of the imprints includes a color display of the new imprint, which, in the examples below, uses the RGB (red, green, blue) system. Thus, in Example 5, for the enantioselectivity of a sample, the results that are obtained from this sample in its reaction with two enantiomers (R) and (S) are accumulated separately. In Example 5, the color green is attributed to the selectivity of the sample for enantiomer S and the color red for enantiomer R.

In these examples, a characteristic that is represented in color form is associated with a triplet of values. However, it is possible to imagine another arrangement of values with which a characteristic would be associated.

Figure 6A:
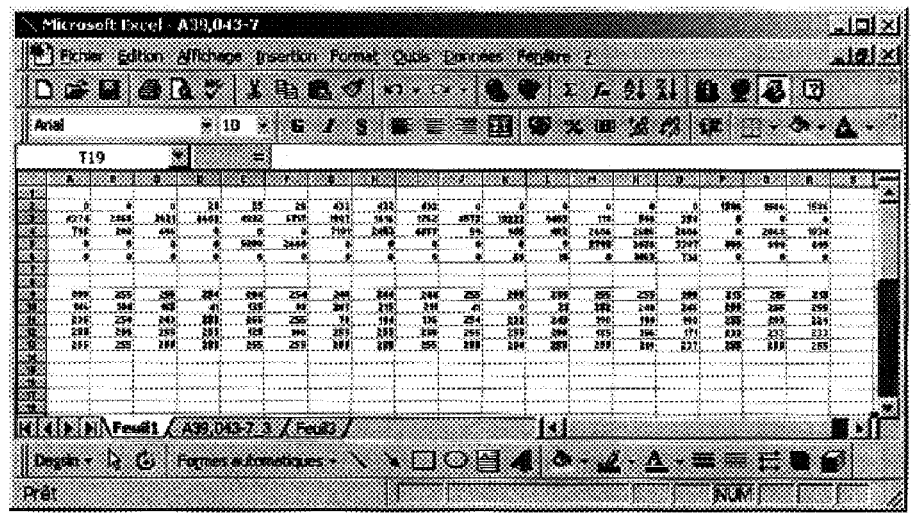
FIG. 6A shows processing of data to obtain relative values.
Figure 6B:
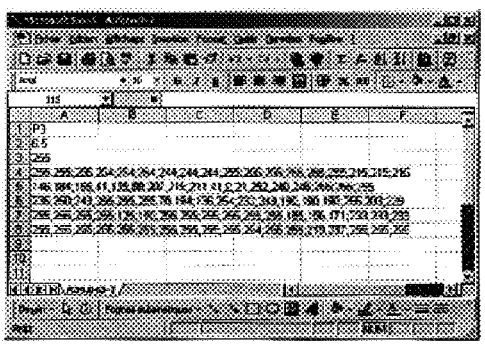
FIG. 6B shows backup up values in a comma separated value(s) (CSV) file format.
Figure 6C:
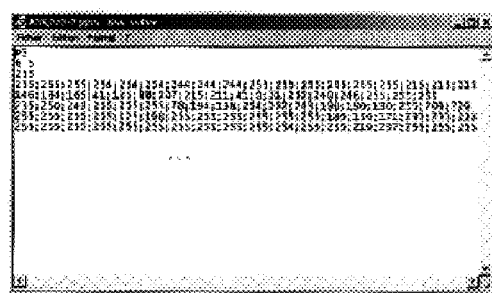
FIG. 6C shows creation of a portable pixel map (PPM) file format.
Figure 6D:
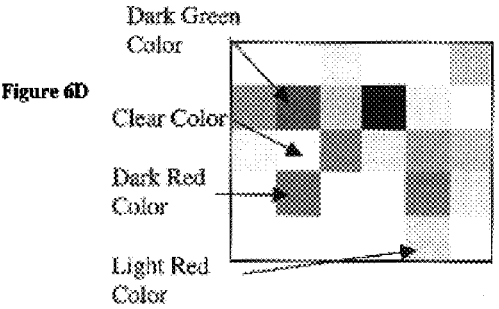
FIG. 6D shows an image of an imprint (in a bitmap (BMP) file).

In general, the imprints are obtained from the raw speed values deducted from the corresponding background noise and reduced to whole values comprised between 0 (no catalytic activity) and 255 (which corresponds to the value of maximum speed in each imprint, stage A shown in FIG. 6A). These integers are then reversed between 255 (maximum luminosity in the scale of 256 colors) and 0 (minimum luminosity), distributed in the desired positions and converted into a CSV (comma separated values) file in Microsoft Excel (stage B shown in FIG. 6B). The CSV file is transformed into a PPM (portable pixel map) file using the Bloc-Notes program of Windows (stage C shown in FIG. 6C), where each triplet of values is converted into one square of 1 pixel with the corresponding color, and the image that is thus obtained is saved as a bitmap file by using the JASC image editor in Paint Shop Pro (stage D shown in FIG. 6D). The imprint, consisting of squares of 1 pixel only, is therefore not only of high quality, but also very easy to use in computer processing. One example of translation of a triplet of values into one color is exhibited in FIG. 7 in the case of the square from the bottom to the left of the imprint.

The implementation of this processing in the case of catalytic measurements comprises:

For one characteristic: the value is reported to be between 0 and 255 relative to the maximum value that is obtained and repeated for each parameter of the RGB system (Example 1).

For two characteristics: each value can be reported to be between 0 and 255 relative to the maximum of all the values, or each value of one normalized characteristic relative to the maximum value of this characteristic; the values that are obtained can then be distributed in one or the other of the parameters of the RGB system, whereby the third parameter is obtained by combining the other two (e.g., mathematical mean, maximum, minimum) (see Example 4).

For three characteristics: each value that corresponds to a characteristic is assigned to a parameter of the RGB system. The selection of the correspondence will have an effect only on the colors that are obtained in the final imprint (e.g., major component in the red, the green or the blue) (see Example 6).

For more than three characteristics: the values that are obtained should be combined mathematically so as to reduce them to at most three different characteristics in the case of a display using the RGB system.

The computer processing of the experimental raw data making it possible to obtain whole numbers between 0 and 255 can be done according to any mathematical formula. The simplest processing remains, however, the normalization of the raw values between 0 and 1, the extrapolation at a 0–255 interval, then the rounding of the values into whole numbers.

The normalization between 0 and 1 can be done by relating the raw values to the same reference number (to their maximum value, for example) in general on the three parameters of the RGB system. It can also be done by modifying the mathematical processing according to the red, green or blue parameter, either by changing the reference number or by distinguishing the decimal values of the raw data (the values between 0 and 10 for red, between 10 and 100 for green, and between 100 and 1000 for blue, for example) or by distinguishing the orders of magnitude by a logarithmic function, for example.

Example 5

Imprints of Enantioselective and Stereoselective Idiosyncratic Catalytic Activities.

The stereoselectivity and enantioselectivity properties of enzymes being important in the synthetic applications, the signals that are recorded in Example 1 are combined to form a color scale from green to red, representing the selectivity of the sample.

In this display, the enantiomeric and stereoisomeric pairs of substrates are combined into a single position. These imprints of selectivity are generated by a combination of speeds that are obtained for the chromogenic and fluorogenic substrates: in the case of an enantiomeric pair, the speed that is obtained for enantiomer R is defined as the value that corresponds to the red component of the RGB (red, green, blue) system for the computer definition of the colors, while the speed that is obtained for enantiomer S corresponds to the green component. The blue component of the RGB system is then simply defined as the mathematical mean of the two other components.

The racemic and achiral substrates are also shown, but in grayscale as described in Example 1, so as to obtain a grid of substrates all resembling the substrates that are described in Example 1.

The substrates are placed in the form of Table 2 below of 5 lines and 6 columns, where the numbering refers to FIGS. 1a and 1b.

TABLE 2

|   | A | B | C | D | E | F |
|---|---|---|---|---|---|---|
| 1 | A1 | B1 | B'3 | C1 | D1 | B'4 |
| 2 | A2/A3 | A'1/A'2 | E2/E3 | C2/C3 | E1/F1 | G2 |
| 3 | B2/B3 | B'1/B'2 | F2/F3 | D2/D3 | G1 | C'1/C'2 |
| 4 | A4/A5 | A'3/A'4 | G4/G5 | B4/B5 | H1/H2 | G3 |
| 5 | C4/C5 | D4/D5 | B4 | E5/F4 | H3/H4 | Ref |

The color key, shown in FIG. 8, indicates the relationship of the tint with the selectivity, and the intensity with the reaction speed.

The idiosyncratic catalytic imprint of selectivity of the generated signals is then displayed as well as the value of the apparent maximum speed in pM/s.

The imprints that are obtained by combination of the results that are cited in Example 1 are shown in FIG. 9. The codes of the different samples tested by imprint are described in Table 1.

These different imprints make it possible to demonstrate, by a simple visual analysis, the stereoselectivity and/or enantioselectivity properties of different samples. For example, the samples referred to as PFL and WGL, which exhibit similar activity imprints, show opposite selectivity imprints. The selectivity of a sample also can vary from one substrate to another, as in the case of the PRL sample where the results are opposite for the substrates that are located in positions C2 and C3 of Table 2.

Example 6

Idiosyncratic Catalytic Activity Imprints with Different pH.

Idiosyncratic catalytic activity imprints reflect different experimental conditions for capturing signals that can be generated, for example, by combining the measurements that are carried out with different pH values on the same grid of phosphatase substrates.

The various fluorogenic substrates, shown in FIG. 10, are tested separately in wells of microtitration plates, in the presence of 4 different phosphatases described in Table 3, with pH levels 2.5, 4.5, 5.5 and 6.5, under the conditions that are described Example 1.

The pH of the measurement solution is then adjusted to 9, the developer agent is added (1 mmol of NaIO4, 2 mg/ml of BSA), and the results are recorded after 1 hour.

The values of fluorescence or absorbence are then converted into concentrations of formed product (umbelliferone or 4-nitrophenol), and these conversion values are recorded at gray levels ranging from white (no conversion) to black (maximum conversion for a sample over all the measurements taken).

The idiosyncratic imprints that are obtained, as well as the percentages of maximum conversion, are shown in FIG. 11. In this case, the activity of the sample, which depends on pH, provides different results according to the substrate and the pH. The combination of all of the data then makes it possible to obtain a specific imprint of the sample according to its activity with different pH values.

TABLE 3

| CIAP | Alkaline Phosphatase of Calf Intestinal Mucous Membrane | 1.4 U/mg |
|---|---|---|
| A. f. | *Aspergillus ficuum* phytase | 3.5 U/mg |
| Novo | Novo phytase | — |
| Natuphos | Natuphos phytase | — |

Example 7

Imprints of Idiosyncratic Catalytic Activities with Various Sample Concentrations.

Imprints of idiosyncratic catalytic activities combining the activities of the sample at different concentrations can likewise be generated by combining, for example, the measurements of lipasic activities of several samples on the same grid of substrates for 3 different concentrations of the sample.

The experimental conditions for capturing signals are the same as those described in Example 1 for a series of chromophoric substrates (FIG. 12). Simply, the concentration of the sample added to the solution is modified such that in the present example, the final concentration of the sample is 100, 10 or 1 microg/ml.

The substrates are placed in the wells of microtitration plates according to the arrangement that is illustrated in FIG. 12. The reaction speeds that are obtained in each case are recorded, then distributed according to the following order:

1) The speeds that are obtained for a concentration of 100 microg/ml are defined as the red component of the RGB system, the maximum speed that is obtained for the sample on the entire grid corresponding to the maximum intensity of red, 2) The speeds that are obtained for a concentration of 10 microg/ml are defined as the green component of the RGB system, the maximum speed that is obtained for the sample on the entire grid corresponding to the maximum intensity of green, 3) The speeds that are obtained for a concentration of 1 microg/ml are defined as the blue component of the RGB system, the maximum speed that is obtained for the sample on the entire grid corresponding to the maximum intensity of blue.

The idiosyncratic imprints that are obtained are shown in FIG. 13. Under each imprint are also recorded the values of maximum speeds obtained on the grid of substrates, at each concentration, and in the following order: 100, 10 and 1 microg/ml.

The results that are obtained according to this processing make it possible to demonstrate the activity of each sample according to its concentration, relative to the same grid of substrates.

In a visual manner, these imprints show the tendency of the catalytic activity based on the dilution of the catalyst, according to the color code that is shown in FIG. 14, established according to Example 4, for each substrate. Furthermore, these same imprints provide an idea of the order of magnitude of the catalytic activity according to the intensity of the color that is obtained.

Another solution consists in wanting to obtain a visualization of the catalytic activity of the sample based on its dilution, but in a general way over the entire grid, by taking into account only the maximum speed that is obtained over all the measurements taken with this sample. The imprints that are thus obtained (FIG. 15) always make it possible to visualize the tendency of the activity based on the concentration, but by focusing the perception on the most active substrates.

Finally, this same processing can be carried out, but by truncating the results that are obtained for the better substrates by omitting the values that are more than 25000 pM/s, which are related to the color black (FIG. 16). Thus, the observations are identical as in the case of FIG. 15, but by broadening the color graduation scale for low speeds (from 0 to 25000 instead of 0 at Vmax).

Example 8

Embodiment of an Imprint of Idiosyncratic Catalytic Activities Starting from a Mixture of Substrates.

It is also possible to produce an imprint by measuring the reaction of each substrate in a series of different substrates that are brought into contact with the sample in the form of a mixture. The reaction by HPLC after a given conversion period is then analyzed. The analysis is particularly simple if all of the products that are formed by the reaction of the different substrates can be easily separated and visualized by HPLC. For example, most of the 1,2-diol or 1,2-amino alcohol derivatives can be easily separated by HPLC, and all of these derivatives produce an intense and specific signal, either the fluorescence at 440 nm, or the UV absorbance at 325 nm, which facilitates their detection by HPLC. Diagram 1 shows a possible series of diols. Diagram 2 shows the separation of five diols by RP–HPLC (Reverse Phase HPLC). The tested reaction is the formation of these products starting from various substrates, which are selected to appear at different retention times in HPLC analysis.

FIG. 17 provides an example of a series of 1,2-diols of diverse structure that can be analyzed by HPLC.

FIG. 18 represents the HPLC trace of a mixture of five diols under the following isocratic conditions: 0.60% ($CH_3CN/H_2O$ 1:1)/40% (0.1% TFA in $H_2O$).

The imprint by mixing is done by analysis of the reaction of at least one mixture of substrates with the sample in the following manner:

The sample is brought into contact with the mixture of substrates;

After a given reaction period, the amount of each product formed by integration of the HPLC peaks of the products is analyzed;

The imprint is produced from amounts of formed products.

The mixtures of substrates comprise between two and one hundred substrates, even one thousand substrates. Each substrate is present at a concentration of between 10 and 200 microM, most particularly 20–50 microM.

It is possible, for example, to use the mixture of three pairs of pseudo-enantiomeric acetates 10/11, 12/13 and 14/15, shown in FIG. 19. The reaction of the mixture gives rise to the formation or otherwise of six products of 1,2-diol type that each provide a different HPLC peak. A simple imprint of esterase activity on acetates is thus produced.

In a second implementation, it is possible to focus on the esterolytic activity based on the nature of the ET carboxylic acid portion of the alcohol portion. For example, the series of 10 ester/carbonate substrates 16–25 shown in FIG. 20 can be used in an equimolar mixture to measure the esterase imprint of a sample. Each engaged substrate provides by hydrolysis a diol-type product that can be identified in the mixture by HPLC analysis.

The concept can be used in a general way by using a variety of functional groups. The structural varieties on the product that are analyzed by HPLC are multiple, such as, for example, with the products 26–31 that are shown in FIG. 21. It is possible to carry out a mixing of substrates with various groups, such as amide, epoxide, ester, carbonate, phosphate, sulfate, epoxide, olefin, etc.

In a general way, it is possible to apply the method for any series of substrates that provide in unique correspondence a series of corresponding products that can be analyzed by analytical separation (GC (gas chromatography, HPLC, MS, NMR (nuclear magnetic resonance)).

Example 9

Imprints of Idiosyncratic Catalytic Activities that are Obtained After HPLC Analysis.

A series of four ester acetate-type substrates 1, 3, 5 and 7 (FIG. 22) is used in an equimolar mixture at a concentration of 0.1 mmol of each substrate. The enzyme (0.05 mg/ml) is incubated with the mixing of substrates at 25° C. for one hour in the phosphate buffer, pH 7.4, containing 1 mg/ml of BSA. The diol-type products 2, 4, 6, and 8 that are formed by the enzymatic hydrolysis reaction are analyzed and quantified by RP-HPLC (Reversed-Phase HPLC. C18, Vydac 218-TP54, 0.5×22 cm, 1.5 ml/min, water/acetonitrile gradient). The starting products are not visible under the selected analysis conditions. This analysis makes it possible to identify the enzyme by a unique spectrum of relative concentration of formed products. The spectra that are obtained can be reproduced and are characteristic of the enzymes used. The four peaks therefore represent the relative concentrations of the four products 2, 8, 4 and 6, in their order of elution (FIG. 23). The HPLC spectra that are obtained are then shown in grid form with four squares (FIG. 24). Thus, the surface area of the peak that is obtained for each of the four products is converted into a grayscale-tinted square.

We claim:

1. A method for generating an idiosyncratic catalytic imprint of a sample having catalytic activity comprising:
   (a) contacting the sample with at least one group of substrates;
   (b) reacting said substrates with the sample for a period of time sufficient for the occurrence of catalytic activity on said substrates, said catalytic activity constituting a signal;
   (c) capturing signals generated by the substrates in an ordered manner to create the idiosyncratic catalytic imprint; and
   (d) using the idiosyncratic catalytic imprint to identify the sample having catalytic activity.

2. The method of claim 1, wherein the substrates comprise sensitivity to degradation, non-specific activities, or a combination thereof.

3. The method of claim 1, wherein the substrates comprise formula (I), formula (II), formula (III), formula (IV), formula (V), or a combination thereof;
   wherein formulas (I) through (V) comprise:

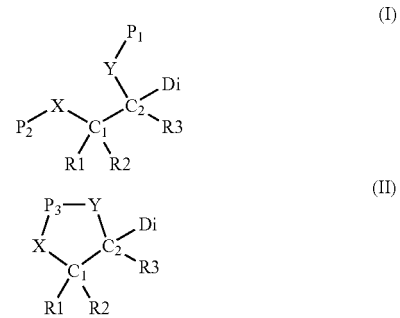

-continued

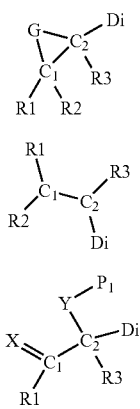

(III)

(IV)

(V)

wherein the $C_1$–$C_2$ bond is insensitive to a cut by a chemical oxidation reaction; Di represents the precursor of a detectable product; X and Y, identical or different, are an oxygen atom, a sulfur atom, or an amine of formula —$NR_{11}R_{12}$–; $R_{11}$ is a hydrogen atom, an alkyl group, or an aryl group, which is optionally substituted, and $R_{12}$ is not a hydrogen atom; R1 to R3, identical or different, are a hydrogen atom, an alkyl group that is optionally substituted, or a chemical group as defined above; $P_1$ and $P_2$, identical or different, are functional groups as defined above, and at most one of groups $P_1$ and $P_2$ is a hydrogen atom; $P_3$ is a carbonyl group, a group —$PO_2R_{11}$ or a group $R_{11}PO$—, where $R_{11}$ has the same meaning as above, a group —$SO_2$, a group —$CHOR_{13}$ wherein $R_{13}$ represents an aryl group, alkyl group or glycosyl group, a group $SiR_{14}R_{15}$, wherein $R_{14}$ and $R_{15}$, identical or different, represent an aryl group, alkyl group, aryloxy group or alkoxy group and a group $AsO_2H$—; and G is an oxygen atom, a sulfur atom, or an amine group of formula $NR_{13}$ where $R_{13}$ is $R_{11}$ or $R_{12}$, $R_{11}$ and $R_{12}$, having the same meaning as above.

4. The method of claim 1, wherein the substrates react over a reaction time of less than or equal to two hours.

5. The method of claim 4, wherein the reaction time is less then or equal to 20 minutes.

6. The method of claim 1, wherein the at least one group of substrates comprises less than 1000 substrates.

7. The method of claim 1, wherein the at least one group of substrates comprises less than 200 substrates.

8. The method of claim 1, wherein the at least one group of substrates comprises ordered substrates.

9. The method of claim 1, wherein the substrates comprise at least one functional group.

10. The method of claim 9, wherein the functional group is sensitive to catalytic activity of the sample.

11. The method of claim 9, wherein the substrates comprise at least one chemical group that imparts a specificity for activity defined by the functional group.

12. The method of claim 11, wherein the substrates comprise different functional groups.

13. The method of claim 11, wherein the substrates comprise different chemical groups.

14. The method of claim 11, wherein the chemical group comprises substitution variations.

15. The method of claim 10, wherein the catalytic activity corresponds to at least one enzyme or mixture of enzymes.

16. The method of claim 10, wherein the catalytic activity is unknown.

17. The method of claim 9, wherein the functional group generates a signal in a direct manner.

18. The method of claim 9, wherein the functional group generates a signal in an indirect manner.

19. The method of claim 1, wherein the signals are all of a same type.

20. The method of claim 1, wherein the signals are captured by measurement with a sensor.

21. The method of claim 1, wherein the signals are captured using a separation technique.

22. The method of claim 21, wherein the separation technique comprises gas chromatography, high-pressure liquid chromatography, mass spectrometry, nuclear magnetic resonance, or a combination thereof.

23. The method of claim 1, wherein the method further comprises assigning each signal a digital value to create the idiosyncratic catalytic imprint.

24. The method of claim 23, wherein the digital value comprises a component of a graphical display.

25. The method of claim 1, wherein the method further comprises analysis of the idiosyncratic catalytic imprint.

26. The method of claim 25, wherein the analysis comprises characterizing or carrying out a follow-up of evolution of the sample.

27. The method of claim 25, wherein the analysis comprises comparing the idiosyncratic catalytic imprint generated at an initial time, $t_0$, with an idiosyncratic catalytic imprint generated at a later time, $t_1$.

28. A method for generating an idiosyncratic catalytic imprint of a sample having catalytic activity comprising:
(a) contacting the sample with at least one group of substrates;
(b) reacting said substrates with the sample for a period of time sufficient for the occurrence of catalytic activity on said substrates, said catalytic activity constituting a signal,
(c) capturing said signals,
(d) converting said signals into catalytic parameters, and
(e) generating an idiosyncratic catalytic imprint by graphical display from said catalytic parameters, wherein a digital value is assigned to each catalytic parameter after normalization between corresponding minima and maxima, wherein a graphical representation system defines minimum and maximum digital values
(f) using the idiosyncratic catalytic imprint to identify the sample having catalytic activity.

* * * * *